United States Patent
Esswein et al.

(10) Patent No.: US 6,429,288 B1
(45) Date of Patent: Aug. 6, 2002

(54) PEPTIDES CONTAINING AN ARGININE MIMETIC FOR THE TREATMENT OF BONE METABOLIC DISORDERS, THEIR PRODUCTION, AND DRUGS CONTAINING THESE COMPOUNDS

(75) Inventors: Angelika Esswein, Büttelborn; Eike Hoffmann, Viernheim; Lothar Kling, Mannheim; Silvia Konetschny-Rapp, Weinheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/486,679

(22) PCT Filed: Sep. 2, 1998

(86) PCT No.: PCT/EP98/05547

§ 371 (c)(1),
(2), (4) Date: Mar. 31, 2000

(87) PCT Pub. No.: WO99/12970

PCT Pub. Date: Mar. 18, 1999

(30) Foreign Application Priority Data

Jun. 5, 1997 (EP) .............................................. 97115402

(51) Int. Cl.[7] .................................................. C07K 5/08
(52) U.S. Cl. ......................... 530/331; 514/17; 514/18; 514/19; 514/20; 530/330; 530/331; 562/553
(58) Field of Search .............................. 514/19, 17, 18, 514/20; 530/330, 331; 562/553

(56) References Cited

FOREIGN PATENT DOCUMENTS

| EP | 0567391 | 10/1993 |
|---|---|---|
| EP | 0616814 | 3/1994 |
| WO | WO 91/18558 | 12/1991 |
| WO | WO 92/10511 | 6/1992 |
| WO | WO 93/00050 | 1/1993 |
| WO | WO 93/20859 | 10/1993 |
| WO | WO 94/24153 | 10/1994 |
| WO | WO 97/21725 | 6/1997 |

OTHER PUBLICATIONS

Valin, et al., J. Cell. Physiol. vol. 170(2) pp. 209–215 (1997).
Whitfield et al., J. Cell. Physiol. vol. 166(1) pp. 1–11 (1996).
Kaji, et al., Endocrinology vol. 136(3) pp. 842–848 (1995).
Macdonald, et al., J. Org. Chem. vol. 48, pp. 1129–1131 (1983).
Fu, et al., J. Am. Chem. Soc., vol. 114, pp. 7324–7325 (1992).
J. Cooper et al., J. Chem. Soc. Perkin Trans 1, pp. 1313–1318, 1993.

*Primary Examiner*—Christopher S. F. Low
*Assistant Examiner*—David Lukton
(74) *Attorney, Agent, or Firm*—George W. Johnston; Dennis P. Tramaloni

(57) ABSTRACT

Arginine mimetic peptides according to Formula I of this application have a stimulating effect on bone formation and are useful for the treatment of bone metabolic disorders.

8 Claims, No Drawings

PEPTIDES CONTAINING AN ARGININE MIMETIC FOR THE TREATMENT OF BONE METABOLIC DISORDERS, THEIR PRODUCTION, AND DRUGS CONTAINING THESE COMPOUNDS

BACKGROUND OF THE INVENTION

The present invention relates to new peptide mimetics for the treatment of bone disorders, methods for their production, and drugs containing these compounds.

In healthy individuals. the formation and degradation processes in the bones are virtually at equilibrium, i.e., the activity of the osteoblasts and osteociasts is balanced. However, if this equilibrium is disturbed in favor of the osteoclasts and/or to the disadvantage of the osteoblasts, a reduction in bone mass and a negative change in bone structure and function will be the result.

Up to now, bone resorption inhibitors such as estrogens, calcitonin and bisphosphonates are primarily used in the treatment of bone metabolic disorders. However, the use of these substances is limited and in addition, does not show the desired effect in all of the cases. Compounds having a stimulating effect on bone formation and contributing to increase an already diminished bone mass are therefore of particular importance in the treatment of bone disorders.

It is known that PTHrP(107-111) and the peptide derivatives thereof have a positive influence on the inhibition of bone resorption (WO 9210511; WO 9424153). However, Valin et al. in J. Cell Physiol. 170(2), 209–15 (1997), describe an anti-proliferative effect of PTHrP(107-111) on UMR106 cells. Whitfield et al. in J. Cell Physiol. 166(1), 1–11 (1996), demonstrate a stimulating effect on the PKC and a modulation of keratinocyte proliferation by PTHrP (107-111), whereas Kali et al. in Endocrinology 136(3), 842–8 (1995), describe a stimulation of the osteoclasts by PTHrP(107-111).

SUMMARY OF THE INVENTION

Surprisingly, it has now been found that the peptide mimetics of the present invention have a stimulating effect on bone formation and thus, are suitable for the general treatment of bone disorders. In particular, they can be used quite well in those cases where bone formation is disturbed, i.e., they are particularly suited for the treatment of osteopenic diseases of the skeletal system, such as osteoporosis, brittle bone disease among others, as well as for the local promotion of bone regeneration and osteoinduction as, e.g., in orthopedic and orthodontic indications, in fracture curing, osteosyntheses, pseudarthroses and for bone implants to become incorporated.

Due to these properties, they are also used in the prophylaxis of osteoporosis.

Moreover, due to their influence on the bone metabolism, drugs containing the peptide mimetics of the present invention as active substances constitute a basis for the local and systemic treatment of rheumatoid arthritis, osteoarthritis and degenerative arthrosis.

The present invention is directed to compounds of general formula (I)

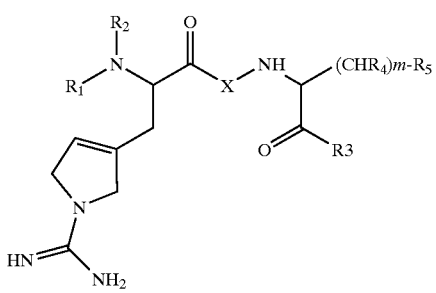

wherein
$R_1$, $R_2$, $R_3$ and X may be the same or different, and wherein $R_1$, $R_2$ represent hydrogen, an amino, peptidyl, alkyl or aryl residue;

$R_3$ represents hydroxy, lower alkoxy, or an —$NR_{31}R_{32}$ residue, where $R_{31}$, $R_{32}$ and represent idependently hydrogen an amino acid, peptidyl, alkyl or aryl residue;

X represents an amino acid or a peptide.

$R_4$ represents hydrogen, hydroxy, amino or $C_1$–$C_4$-alkyl;

m represents a number between 0 and 5;

$R_5$ represents an optionally substituted saturated or unsaturated mono- or bicyclic moiety which may contain one or more heteroatoms, a $C_1$–$C_{11}$ alkyl group which may have substitutions or intermittent heteroatoms;

their tautomers, optical isomers, pharmaceutically acceptable salts and prodrugs.

X is preferably a ω-Amino acid or the dipeptide serinylalaryl;

$R_4$ represents preferably methyl or hydroxy;

$R_1$ and $R_2$ are independently of each other preferably hydrogen;

$R_3$ is preferably hydroxy or amino;

m is preferably 1 to 3, more preferably 1;

The residue $(CHR_4)mR_5$ represents especially preferred a residue attached to Cα of a proteinogenic or non-proteinogenic amino acid.

DETAILED DESCRIPTION OF THE INVENTION

Alkaline salts, earth alkaline salts like Ca or Mg salts, ammonium salts, acetates or hydrochlorides are mainly used as pharmacologically acceptable salts which are produced in the usual manner e.g. by tritrating the compounds with inorganic or organic bases or inorganic acids such as e.g. sodium hydroxide, potassium hydroxide, aqueous ammonia, $C_1$–$C_4$-alkyl-amines such as e.g. triethylamine or hydrochloric acid. The salts are usually purified by reprecipitation from water/acetone.

Prodrugs of the compounds of the invention are such which are converted in vivo to the pharmacological active compound. The most common prodrugs are carboxylic acid esters, like ethylesters.

Peptidyl represents are peptide residue. Peptide is understood to be a residue consisting of 2 to 10 proteinogenic or non-proteinogenic identical or different amino acids. Peptides having 2–5 amino acids are preferred; particularly preferred are those having 2 amino acids.

Amino acid residue normally means the residue of a proteinogenic or non-proteinogenic amino acid. Non-proteinogenic amino acids are understood to be α-, β-, γ-, and ω-aminocarboxylic acids which may optionally have substitutions or intermittent heteroatoms.

Preferred ω-amino acids are —HN—(CH$_2$)$_n$—CO— with n=1–10; the —(CH$_2$)$_n$-group may be branched or unbranched.

Examples of such amino acids are the L- and D-amino acids, like 2-amino-3-hydroxy-4-methylpentanoic acid, 2-amino-3-hydroxy-4-methylpentanoic acid, 2-amino-3-methoxybutanoic acid, 2,3-diaminopropionic acid, 2-amino-2-methyl-3-hydroxypropanoic acid, 2-amino-2-methylbutanedioic acid, 2-amino-3-hydroxy-3-methylbutanoic acid, 2-amino-3-hydroxy-3-methylbutanoic acid, 2,3-diaminopropionic acid, 2-amino-2-methyl-3-hydroxypropanoic acid, 2-amino-2-methylbutanedioic acid, 2-amino-2-methylbutanoic acid, 2-amino-2-methyl-4-pentenoic acid, 2-amino-3-methoxypropanoic acid, 1-amino-1-cyclohexanecarboxylic acid, 1-amino-1-cyclopentanecarboxylic acid, 1-aminocyclobutanecarboxylic acid, 1-aminocyclopropanecarboxylic acid, 2-(2-furyl)glycine, 2-amino-3-fluorobutyric acid, 2-aminoisobutyric acid, 3-chloroalanine, 3-fluoronorleucine, 3-fluorovailne, 3-fluoroalanine, 3-methoxyvaline, alpha-cyanoalanine, alpha-methylleucine, beta-chloroalanine, beta-cyanoalanine, beta-hydroxyleucine, beta-hydroxyaspartic acid, 3-hydroxyaspartic acid, 2-aminobutyric acid, allylglycine, gamma-methylleucine, homoserine, norleucine, norvaline, tert-leucine, 2,3-diaminopropionic acid, 2,3-diaminosuccinic acid, 2-amino-4-pentenoic acid, 2-aminobutyric acid. 2-aminoheptanoic acid, 2-cyclopropyl-2-methylglycine, 4-thiaisoleucine, allothreonine, alpha-methylaspartic acid, alpha-methylserine, beta-hydroxynorvaline, beta-methylaspartic acid, homocysteine, homoserine, norleucine, norvaline, O-methylserine, penicillamine, propargaylglycine, beta-hydroxyaspartic acid vinylglycine, beta-hydroxyaspartic acid, H-4,5-dehydro-LEU-OH, H-alpha-MeVAL-OH, H-propargayl-GLY-OH, H-allo-ILE-OH, H-PRA-OH, H-trans-4,5-dehydroLYS-OH, 3-hydroxyaspartic acid, 6-hydroxynorleucine, allo-isoleucine, allyl glycine, alpha-amino-N-butyric acid, gamma-methylleucine, homoserine, norvaline, penicillamine, tert-leucine, vinylglycine, meso-alpha beta-diaminosuccinic acid, O-carbamoyl-serine, S-methylcysteine, 2-amino-2-methylbutanedioic acid, 2-fluoro-beta-alanine, beta-alanine, beta-aminobutyric acid, 2,3-diaminosuccinic acid, beta-aminoisobutyric acid, isoserine, Preferred amino acids are alanine, serine, tryptophan, tyrosine, phenylalanine, threonine, histidine, citrulline, homocysteine, homoserine, hydroxyproline, hydroxylysine, ornithine, sarcosine, tranexamic acid, Cha (cyclohexylalanine), aminobutyric acid, aminovaleric acid, and aminopropionic acid.

Lower alkoxy denote methoxy, ethoxy, propoxy, ispropoxy or butoxy, preferably methoxy.

Alkyl normally means linear or branched alkyl residues having from one to six carbon atoms.

Aryl normally means a carbocyclic moiety having from 6 to 14 C atoms or a 5- or 6-membered heterocyclic moiety having 1, 2 or 3 heteroatoms selected from O, N, S, which moiety may optionally have one or multiple substitutions, with unsubstituted or optionally substituted phenyl or naphthyl residues being preferred.

Monocyclic moiety is understood to be a saturated or unsaturated ring system having 3–8, preferably 5–7 carbon atoms, which may optionally have one or multiple intermittent heteroatoms such as nitrogen, oxygen or sulfur, particularly a cyclopentyl, cyclohexyl, cycloheptyl, morpholinyl, thiamorpholinyl, piperidinyl, piperazinyl, tetrahydrofuranyl, tetrahydropyranyl, phenyl, pyridyl, pyrimidinyl, pyridazinyl, pyrazinyl, furyl, thiophenyl, imidazolyl, thiazolyl, oxazolyl, isothiazolyl, isoxazolyl, 1,2,3-triazolyl, or 1,2,4-triazolyl residue. In particular, lower alkyl, alkoxy and halogen are possible as substituents.

Preferably, the bicyclic moiety referred to under R$_5$ is a residue such as a naphthyl, tetrahydronaphthyl, decalinyl, quinolinyl, isoquinolinyl, tetrahydroquinolinyl, tetrahydroisoquinolinyl, indolyl, benzimidazolyl, indazolyl, oxindolyl, benzofuranyl, benzothiophenyl, benzothiazolyl, benzoxazolyl or purinyl residue, but particularly an indolyl, naphthyl, benzimidazolyl, quinolinyl, tetrahydroquinolinyl, benzothiophenyl, and benzofuranyl residue.

The term "several" means in connection with heteroatoms in monocycles or bicycles preferred one, two or three more preferred one or two, the most preferred heteroatom is nitrogen.

The term "several" means in connection with substituents or substitution preferred one to five, more preferred one, two or three most preferred one or two.

Substitutions of monocycles or bicycles in R$_5$ are halozen. nitro, hydroxy, alkoxy, amino, alkylamino, dialkylamino, halogenmethyl, dihalogenmethyl, trihalogenmethyl, phosphono, alkylphosphono, dialkylphosphono, SO$_2$NH$_2$, SO$_2$NH(alkyl), SO$_2$N(alkyl)$_2$, S$_2$(alkyl), acetyl, formyl, nitril, COOH, COOalkyl, —OC(O)alkyl, —NHC(O)Oalkyl, OC(O)O—aryl, —NHC(S)NH$_2$, —NHC(S)NHalkyl, —NHC(O)—aryl.

Preferred substituents are methyl, ethyl, propyl, isopropyl, halogenyl, especially chloro, amino, acetyl, alkylamino, dialkylamino, alkoxy, hydroxyalkyl, and C$_0$–C$_4$ alkylcarbonic acids.

The preparation of the compounds of general formula (I) is achieved according to per se known methods. Advantageously, the preparation is effected using the precursors (II), (III) and (IV), respectively,

(II)

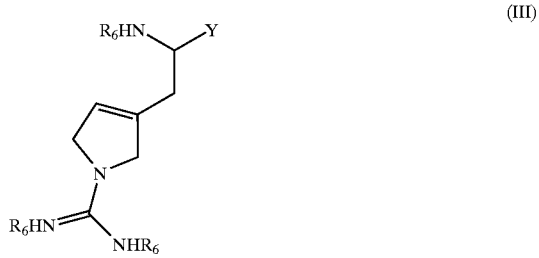

(III)

-continued
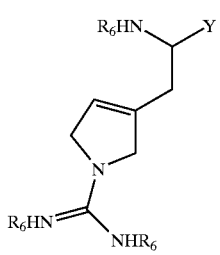
(IV)
wherein Y represents a carboxyl group, according to the procedure outlined in Schemes 1, 2 and 3.
Compounds of general formula (IV) are new and useful for orthogonal syntheses of compounds which comprise the backbone structure of (IV). The preferred residue for $R^9$ is Fmoc.
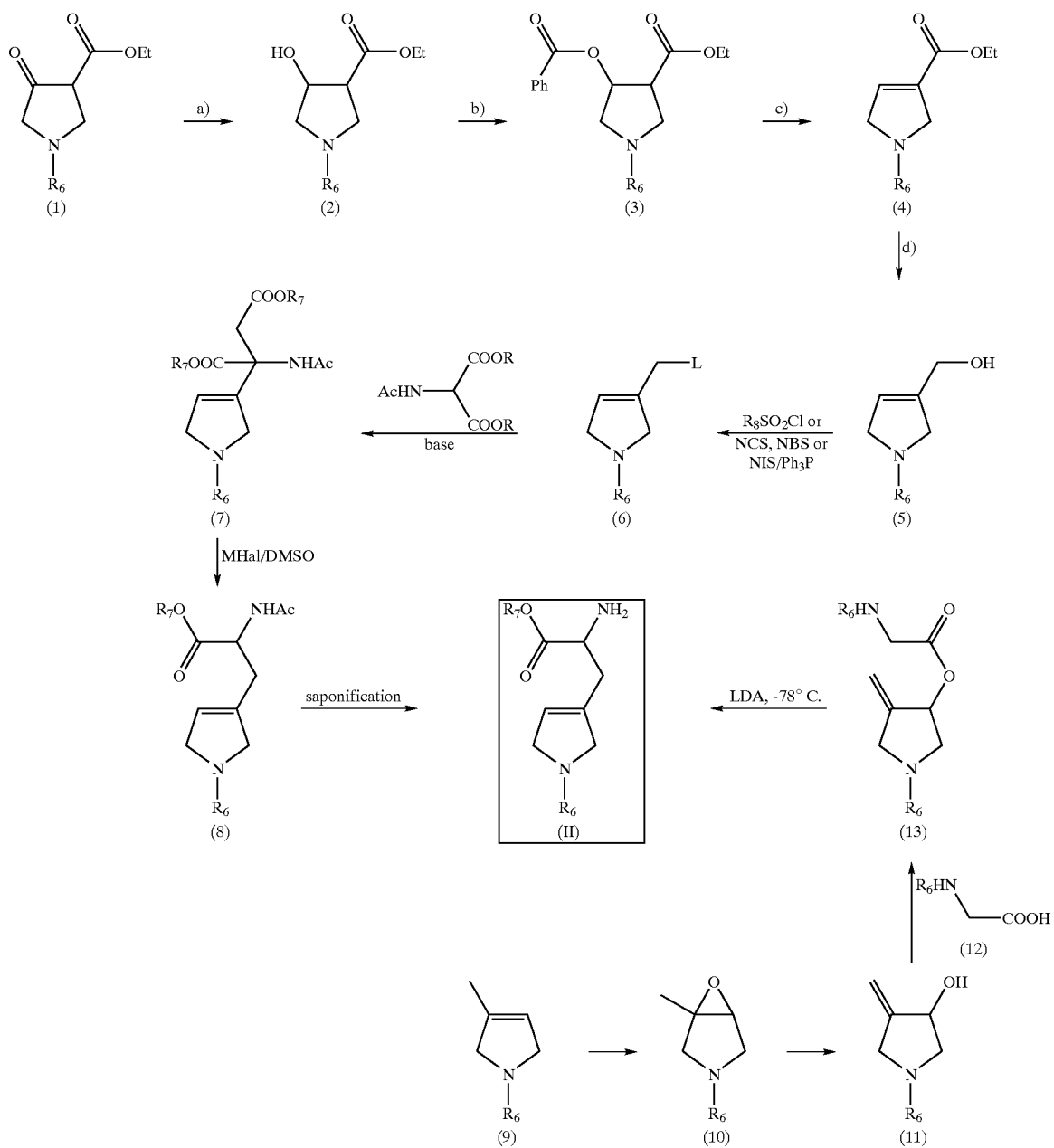

Steps a) through d) in Scheme 1 represent the following reactions:

a) NaBH$_3$CN/MeOH/RT;
b) PhCOCl/py/DMAP/RT;
c) DBU/toluene/RT/16 hrs;
d) DIBAL-H/THF/−78° C.;

wherein R$_6$ represents a protecting group, e.g., the benzoyl group, an alkyloxycarbonyl group or the benzyloxycarbonyl group, and R$_7$ represents hydrogen or lower alkyl such as methyl, ethyl, propyl, butyl or tert-butyl, R$_8$ represents an alkyl or aryl residue such as a methyl, ethyl, trifluoromethyl, phenyl, tosyl or the 4-nitrophenyl residue, but preferably the methyl or tosyl residue, and L normally represents a sulfonic acid residue such as the methane- or trifluoromethane-sulfonic acid or the p-toluenesulfinic acid residue, or halogen such as chlorine, bromine, iodine, or acetate.

MHal represents a metal halide such as NaCl, NaBr, KI, MgCl$_2$ or MgBr$_2$.

Compounds of formula (5) have been described (J.O.C. 48, 1129–31 (1983)). The conversion of an alcohol of formula (5) to a sulfonic or acetic ester of formula (6) is effected according to standard procedures. The transformation of an alcohol of formula (5) into a halide of formula (6) using N-chloro-, N-bromo- or N-iodosuccinimide (NCS, NBS, NIS) in the presence of triphenylphosphine (Ph$_3$P) is performed in analogy to the corresponding literature procedures (e.g., Tetrahedron Asym. 4, 1619–24 (1993)). The decarboxylation of malonic esters using metal halides in DMSO at elevated temperatures is well-known (T.L. 957 (1973)). Compounds of formula (9) have been described (JACS 114, 7324–25 (1992)). The epoxide opening of a compound of formula (10) to yield an allyl alcohol of formula (11) is carried out in analogy to the literature (Tetrahedron 24, 5827–30 (1968)). The conversion of a compound of formula (13) to a compound of general formula (II) by means of a Claisen rearrangement is performed in analogy to the literature (Tetrahedron 52, 941–54 (1996)).

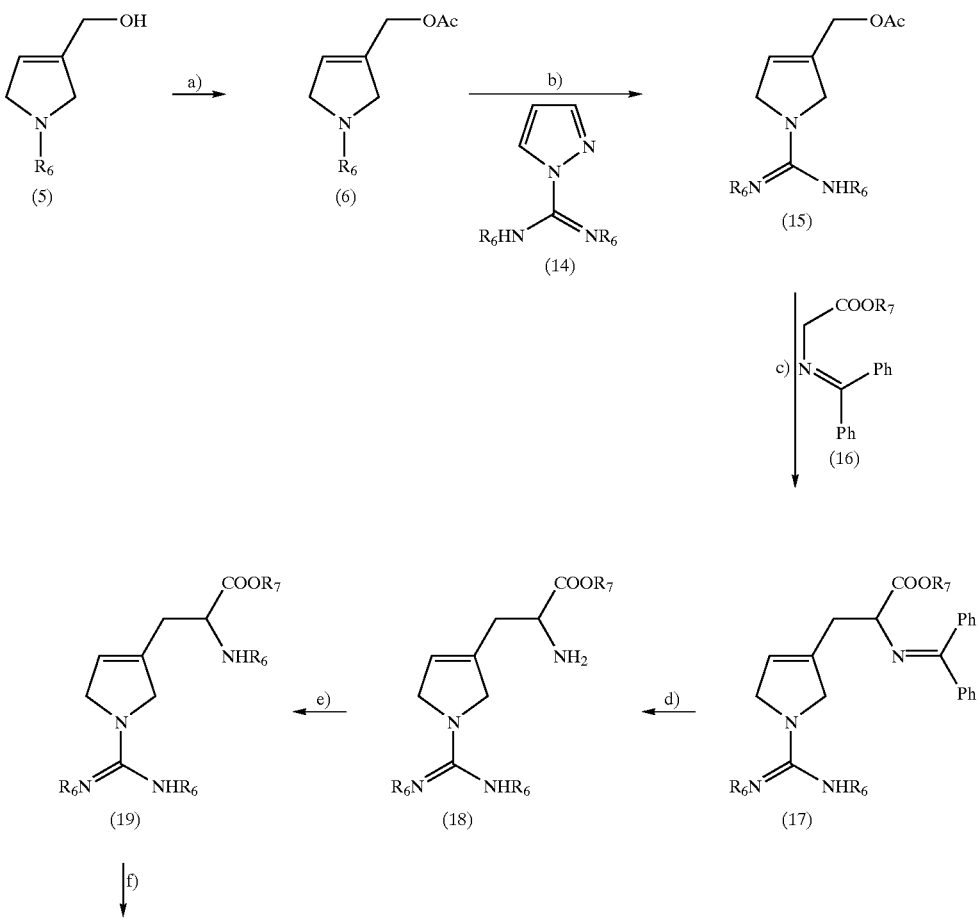

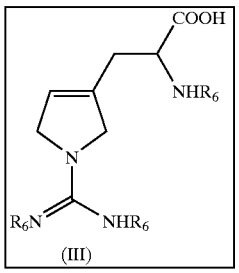
(III)

Step a) through f) in Scheme 2 represent the following reactions:
a) Ac$_2$O/pyridine/DMAP
b) 4 N HCl/16 hrs; (14)/EtN(i-Pr)$_2$
c) (16), R$_7$ = Et/HMDS/n-BuLi/-78° C.
d) 1 N HCl/THF/RT/30 minutes
e) Boc$_2$O/EtN(i-Pr)$_2$/acetonitrile/16 hrs
f) LiOH/THF-MeOH—H$_2$O Steps a) through f) in Scheme 2 represent the following reactions:
a) Ac$_2$O/pyridine/DMAP
b) 4 N HCl/16 hrs; (14)/EtN(i-Pr)$_2$
c) (16), R$_7$=Et/HMDS/n-BuLi/-78° C.
d) 1 N HCl/THF/RT/30 minutes
e) Boc$_2$O/EtN(i-Pr)2/acetonitrile/16 hrs
f) LiOH/THF-MeOH-H$_2$O
wherein R$_6$ and R$_7$ have the above-mentioned meanings.

d) 4 N HCl/dioxane
e) EtN(i-Pr)$_2$/acetonitrile
wherein R$_6$ and R$_7$ have the above-mentioned meanings and R$_9$ represents another protecting group such as Fmoc or Troc.

The compounds of formula (I) may be administered in liquid or solid form or as aerosols on the oral, enteral, parenteral, topical, nasal, pulmonary or rectal routes in all the common non-toxic, pharmaceutically accepted carriers. adjuvants and additives. The compounds of formula (I) may also be applied locally on/in bones (optionally with surgical operation). The term "parenteral" includes subcutaneous, intravenous and intramuscular supply or infusions. Oral administration forms may be, e.g., tablets, capsules, coated tablets, syrups, solutions, suspensions, emulsions, elixirs, Scheme 3

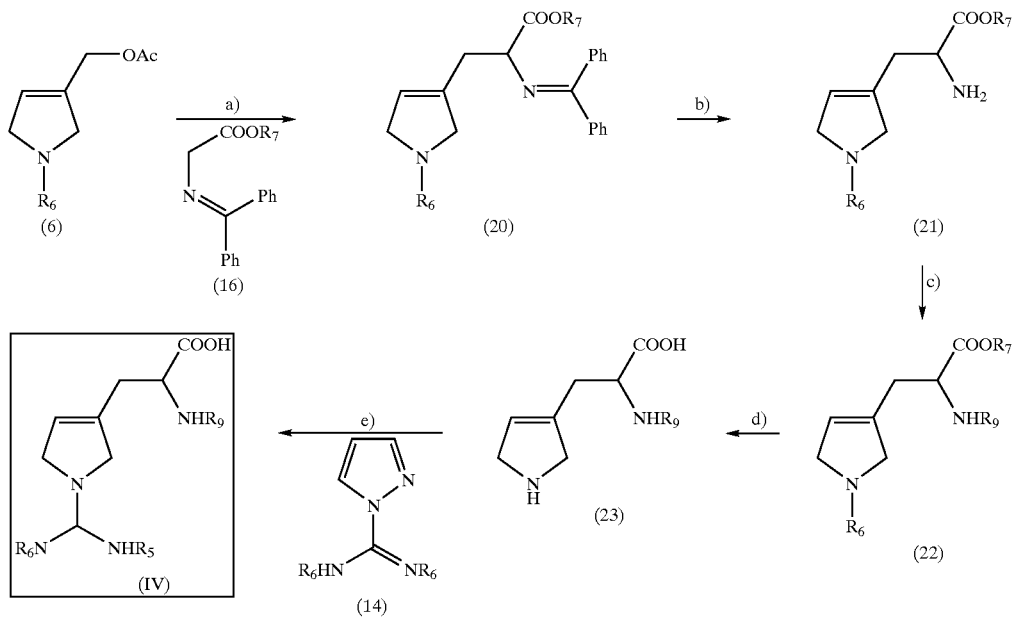

Step a) through e) in Scheme 3 represent the following reactions:
a) HDMS/n-BuLi/-78° C.
b) CH$_3$COOH/THF/RT/30 minutes
c) R$_9$Cl/EtN(i-Pr)$_2$/THF/16 hrs
d) 4 N HCl/dioxane
e) EtN(i-Pr)$_2$/acetonitrile Steps a) through e) in scheme represent the following reactions:
a) HDMS/n-BuLi/-78° C.
b) CH$_3$COOH/THF/RT/30 minutes
c) R$_9$Cl/EtN(i-Pr)$_2$/THF/16 hrs etc., which may contain one or more additives from the following groups, e.g., flavoring substances, sweeteners, colorants. and preservatives. Oral administration forms contain the active component together with non-toxic, pharmaceutically accepted carriers suitable for the production of tablets, capsules, coated tablets, etc. such as calcium carbonate, sodium carbonate, lactose, calcium phosphate or sodium phosphate; starch, mannitol, methylcellulose, talc, highly dispersed silicic acids, higher molecular weight fatty acids (such as stearic acid), peanut oil, olive oil, paraffin, Miglyol, gelatin, agar-agar, magnesium stearate, beeswax, cetyl alcohol, lecithin, glycerol, animal and vegetable fat, solid high molecular weight polymers (such as polyethylene glycols). Tablets, capsules, coated tablets, etc. may be provided with an appropriate coating such as glyceryl monostearate or glyceryl distearate, so as to prevent undesirable side effects in the stomach, or to result in prolonged activity due to delayed absorption in the gastrointestinal tract. Sterile injectable aqueous or oily solutions or suspensions are preferably used as injection media, which contain common additives such as stabilizers and solubilizers. Such additives may be, e.g., water, isotonic saline solution, 1,3-butanediol, fatty acids (such as oleic acid) mono- and diglycerides, or Miglyol. For rectal administration, all the suitable non-irritating additives may be used which are solid at normal temperatures and liquid at rectal temperature, such as cocoa butter and polyethylene glycol. For aerosol administration, the pharmaceutically common carrier media are used. For external application, creams, tinctures, gels, solutions or suspensions with pharmaceutically common additives are used. The dosage may depend on various factors such as the mode of application, species, age and/or individual condition. The doses administered daily or at intervals are around 1–1000 mg/person, preferably around 10–250 mg/person and may be ingested at one go or distributed over several times.

The compounds of formula (I) may be applied locally on/in bones (optionally with surgical operation). The application directly on/in bones (optionally with surgical operation) may be effected either in solution or suspension, conveniently by infusion or injection, locally or carrier-bound. For example, carrier-bound compounds of formula (I) may be applied as gels, pastes, solids or as coating on implants.

As carriers, biocompatible and preferably, biodegradable materials are used. Preferably, the materials themselves will additionally induce wound healing or osteogenesis.

For local application it is preferred to embed the compounds of formula (I) in polymeric gels or films, thereby immobilizing them, and to apply these preparations directly on the point of the bone to be treated. These polymeric base gels or films consist of, e.g., glycerol, methylcellulose, hyaluronic acid, polyethylene oxides and/or polyoxamers. Collagen, gelatin and alginates are also suitable and are described in WO 93/00050 and WO 93/20859, for example. Other polymers are polylactic acid (PLA) and copolymers of lactic acid and glycolic acid (PLPG) (Hollinger et al., J. Biomed. Mater. Res. 17 71–82 (1983)), and the "Demineralized Bone Matrix" (DBM) bone derivative (Guterman et al., Kollagen Rel. Res. 8, 419–4319 (1988)). Polymers such as those used for adsorbing TGFB, for example, are also suitable and are described in EP-A 0,616,814 and EP-A 0,567,391. as well as the synthetic bone matrices according to WO 91/18558.

Materials commonly used when implanting bone substitutes or other therapeutically active substances are also suitable as carriers for the compounds of formula (I). Such carriers are also based on, e.g., calcium sulfate, tricalcium phosphate, hydroxyapatite and its biodegradable derivatives, and polyanhydrides. Apart from these biodegradable carriers, those carriers are also suitable which are not biodegradable but are biocompatible. For example, these carriers are sintered hydroxyapatite, bioglass, aluminates or other ceramic materials (e.g., calcium aluminate phosphate). Preferably, these materials are used in combination with said biodegradable materials, such as, in particular, polylactic acid, hydroxyapatite, collagen, or tricalcium phosphate. Other non-degradable polymers have been described in the U.S. Pat. No. 4,164,560, for example.

Particularly preferred is the use of carriers which continuously release the compounds of formula (I) at the site of action. Especially suited for this purpose are, e.g., the "slow release pellets" by Innovative Research of America, Toledo, Ohio, USA. Particularly preferred is the use of pellets releasing the compounds of formula (I) over several days, preferably up to 100 days, at a daily dose of 1–10 mg/kg per day.

Apart from the compounds mentioned in the examples, and the compounds which may be derived by combining all the meanings of the substituents mentioned in the claims, the following derivatives, as well as their pharmacologically acceptable salts, particularly the hydrochlorides and trifluoroacetates are preferred in the meaning of the present invention.

Index of abbreviations used:
Aba=aminobutyric acid
Ac=acetyl
Ada=(1-amidino-2,5-dihydro-1H-pyrrol-3-yl)alanine
Ala=aanine
Ava=aminovaleric acid
Bn=benzyl
Boc=tert-butyloxycarbonyl
Bu=butyl
Cbz=benzyloxycarbonyl
Cha=cyclohexylalanine
DBU=1,8-diazabicyclo[5.4.0]undec-7-ene
DIBAL-H=diisobutylaluminum hydride
DMAP=4-dimethylaminopyridine
DMF=dimethylformamide
Et=ethyl
Fmoc=9-fluorenylmethoxycarbonyl
Gly=glycine
HMDS=hexamethyldisilazane
i-Pr=isopropyl
Me=methyl
NMM=N-methylmorpholine
Ph=phenyl
Phe=phenylalanine
Pro=proline
py=pyridine
RT=room temperature
Ser=serine
t-Bu=tert-butyl
TBTU=2-(1H-benzotriazol-1-yl)-1,1,3,3-tetramethyluronium tetratfluoroborate
TCP=trityl chloride-polystyrene
THF=tetrahydrofuran
Thr=threonine Troc=2,2,2-trichloroethoxycarbonyl
Trp=tryptophan
Tyr=tyrosine
'B=retention time
Val=valine In addition the one-letter code for amino acids is used.

Within the sense of the present invention the following peptide mimetics are preferred in addition to the compounds mentioned in the examples and compounds that can be derived by combining all meanings of substituents mentioned in the claims in the preferred compounds.

Preferred compounds:

1) 2-{5-[2-(2-Amino-3-hydroxy-butyrylamino)-3-(1-carbamimidoyl-2,5-dihydro-pyrrol-3-yl)-propionylamino]-pentanoylamino}-3-(indol-2-yl)-propionic acid
2) 2-{5-[2-Amino-3-(1-carbamimidoyl-2,5-dihydro-pyrrol-3-yl)-propionylamino]-pentanoylamino}-3-(7-methyl-indol-2-yl)-propionic acid
3) 2-{5-[2-(2-Amino-3-hydroxy-butyrylamino)-3-(1-carbamimidoyl-2,5-dihydro-pyrrol-3-yl)-propionylamino]-pentanoylamino}-3-benzo[b]thiophen-2-yl-propionic acid
4) 2-{5-[2-Amino-3-(1-carbamimidoyl-2,5-dihydro-pyrrol-3-yl)-propionylamino]-pentanoylamino}-3-(6-methyl-indol-2-yl)-propionic acid
5) 2-{5-[2-(2-Amino-3-hydroxy-butyrylamino)-3-(1-carbamimidoyl-2,5-dihydro-pyrrol-3-yl)-propionylamino]-pentanoylamino}-3-(6-hydroxy-indol-2-yl)-propionic acid
6) 2-{5-[2-Amino3-(1-carbamimidoyl-2,5-dihydro-pyrrol-3-yl)-propionylamino]-pentanoylamino}-3-(3-methyl-indol-2-yl)-propionic acid
7) 2-{5-[2-(2-Amino-3-hydroxy-butyrylamino)-3-(1-carbamimidoyl-2,5 -dihydro-pyrrol-3-yl)-propionylamino]-pentanoylamino}-3-(3-methyl-benzofuran-2-yl)-propionic acid
8) 2-{5-[2-Amino-3-(1-carbamimidoyl-2,5-dihydro-pyrrol-3-yl)-propionylamino]-pentanoylamino}-3-(3,4dimethyl-benzofuran-2-yl)-propionic acid
9) 2-{5-[2-(2-Amino-3-hydroxy-butyrylamino)-3-(1-carbamimidoyl-2,5-dihydro-pyrrol-3-yl)-propionylamino]-pentanoylamino}-3-(3,5-dimethyl-benzoruran-2-yl)-propionic acid
10) 2-{5-[2-Amino-3-(1-carbamimidoyl-2,5-dihydro-pyrrol-3-y1)-propionylamino]-pentanoylamino}-3-(3,6-dimethyl-benzofuran-2-yl)-propionic acid
11) 2-{5-[2-(2-Amino-3-hydroxy-butyrylamino)-3-(1-carbamimidoyl-2,5 -dihydro-pyrrol-3-yl)-propionylamino]-pentanoylamino}-3-(5-ethyl-3-methyl-benzofuran-2-yl)-propionic acid
12) 2-{5-[2-Amino-3-(1-carbamimidoyl-2,5-dihydro-pyrrol-3-yl)-propionylamino]-pentanoylamino}-3-hydroxy-3-(3-methyl-benzofuran-2-yl)-propionic acid
13) 2-{5-[2-(2-Amino-3-hydroxy-butyrylamino)-3-(1-carbamimidoyl-2,5-dihydro-pyrrol-3-yl)-propionylamino]-pentanoylamino}-3-(3,7-dimethyl-benzofuran-2-yl)-propionic acid
14) 2-{5-[2-Amino-3-(1-carbamimidoyl-2,5-dihydro-pyrrol-3-yl)-propionylamino]-pentanoylamino}-3-(7-ethyl-3-methyl-benzofuran-2-yl)-propionic acid
15) 2-{5-[2-(2-Amino-3-hydroxy-butyrylamino)-3-(1-carbamimidoyl-2,5-dihydro-pyrrol-3-yl)-propionylamino]-pentanoylamino}3-(3,6-(3,6-dimethyl-benzofuran-2-yl)3-hydroxy-propionic acid
16) 2-{5-[2-Amino-3-(1-carbamimidoyl-2,5-dihydro-pyrrol-3-yl)-propionamino]-pentanoylamino}-3-(3,5-dimethyl-benzofuran-2-yl)-3-hydroxy-propionic acid
17) 2-{5-[2-(2-Amino-3-hydroxy-butyrylamino)-3-(1-carbamimidoyl-2,5-dihydro-pyrrol-3-yl)-propionylamino]-pentanoylamino}3-(3,4-dimethyl-benzofuran-2-yl)-3-hydroxy-propionic acid
18) 2-{5-[2-Amino-3-(1-carbamimidoyl-2,5-dihydro-pyrrol-3-yl)-propionylamino]-pentanoylamino}-3-(3,7-dimethyl-benzofuran-2-yl)-3-hydroxy-propionic acid
19) 2-{5-[2-(2-Amino-3-hydroxy-butyrylamino)-3(1-carbamimidoyl-2,5-dihydro-pyrrol-3-yl)-propionylamino]-pentanoylamino}-3-(7-chloro-3-methyl-benzofuran-2-yl)-3-hydro propionic acid
20) 2-{5-[2-Amino-3-(1-carbamimidoyl-2,5-dihydro-pyrrol-3-yl)-propionylamino]-pentanoylamino}-3-(5-ethyl-3-methyl-benzofuran-2-yl)-3-hydroxy-propionic acid
21) 2-{5-[2(2-Amino-3-hydroxy-butyrylamino)-3-(1-carbamimidoyl-2,5-dihydro-pyrrol-3-yl)-propionylamino]-pentanoylamino}-3-(7-ethyl-3-methyl-benzofuran-2-yl)-3-hydroxy-propionic acid
22) 2-{5-[2-Amino-3-(1-carbamimimdoyl-2,5-dihydro-pyrrol-3-yl)-propionylamino]-pentanoylamino}-3-furan-2-yl-propionic acid
23) 2-{5-[2-(2-Amino-3-hydroxy-butyrylamino)-3(1-carbamimidoyl-2,5-dihydro-pyrrol-3-yl)-propionylamino]-pentanoylamino}-3-furan-2-yl-3-hydroxy-propionic acid
24) {5-[2-Amino-3-(1-carbamimidoyl-2,5-dihydro-pyrrol-3-yl)-propionylamino]-pentanoylamino}-thiophen-2-yl-acetic acid
25) 2-{5-[2-(2-Amino-3-hydroxy-butyrylamino)-3-(1-carbamimidoyl-2,5-dihydro-pyrrol-3-yl)-propionylamino]-pentanoylamino}-3-thiophen-2-yl-propionic acid
26) 2-{5-[2-Amino-3-(1-carbamimidoyl-2,5-dihydro-pyrrol-3-yl)-propionylamino]-pentanoylamino}-3-(pyrrol-2-yl)-propionic acid
27) 2-{5-[2-(2-Amino-3-hydroxy-butyrylamino)-3-(1-carbamimidoyl-2,5-dihydro-pyrrol-3-yl)-propionylamino]-pentanoylamino}-3-(5-methyl-thiophen-2-yl)-propionic acid
28) 2-{5-[2-Amino-3-(1-carbamimidoyl-2,5-dihydro-pyrrol-3-yl)-propionylamino]-pentanoylamino}-3-hydroxy-3-(5-methyl-thiophen-2-yl)-propionic acid
29) 2-{5-[2-(2-Amino-3-hydroxy-butyrylamino)-3-(1-carbamimidoyl-2,5-dihydro-pyrrol-3-yl)-propionylamino]-pentanoylamino}-3-(5-ethyl-thiophen-2-yl)-propionic acid
30) 2-{5-[2-Amino-3-(1-carbamimidoyl-2,5-dihydro-pyrrol-3-yl)-propionylamino]-pentanoylamino}-3-(5-propyl-thiophen-2-yl)-propionic acid
31) 2-{5-[2-(2-Amino-3-hydroxy-butyrylamino)-3-(1-carbamimidoyl-2,5-dihydro-pyrrol-3-yl)-propionylamino]-pentanoylamino}-3-(5-hydroxymethyl-furan-2-yl)-propionic acid
32) 5-(2-{5-[2-Amino-3-(1-carbamimidoyl-2,5-dihydro-pyrrol-3-yl)-propionylamino]pentanoylamino}-2-carboxy-ethyl)-2-methyl-furan-3-carboxylic acid
33) 5-(2-{5-[2-(2-Amino-3-hydroxy-butyrylamino)-3-(1-carbamimidoyl-2,5-dihydro-pyrrol-3-yl)-propionylamino]-pentanoylamino}-2-carboxy-ethyl)-2-ethyl-furan-3-carboxylic acid
34) 5-(2-{5-[2-Amino-3-(1-carbamimidoyl-2,5-dihydro-pyrrol-3-yl)-propionylamino]-pentanoylamino}-2-carboxy-ethyl)-2-methyl-pyrrol-3-carboxylic acid ethyl ester
35) 5-(2-{5-[2-(2-Amino-3-hydroxy-butyrylamino)-3-(1-carbamimidoyl-2,5-dihydro-pyrrol-3-yl)-

36) 3-(5-Acetylimino-4,5-dihydro-thiophen-2-yl)-2-{5-[2-Amino-3-(1-carbamimidoyl-2,5-dihydro-pyrrol-3-yl)-propionylamino]-pentanoylamino}3-hydroxy-propionic acid
37) 5-(2-{5-[2-(2-Amino-3-hydroxy-butyrylamino)-3-(1-carbamimidoyl-2,5-dihydro-pyrrol-3-yl)-propionylamino]-pentanoylamino}-2-carboxy-ethyl)-2-isobutyl-furan-3-carboxylic acid
38) 2-{5-[2-Amino-3-(1-carbamimidoyl-2,5-dihydro-pyrrol-3-yl)-propionylamino]-pentanoylamino}-3-cyclopent-1-enyl-propionic acid
39) 2-{5-[2-(2-Amino-3-hydroxy-butyrylamino)-3-(1-carbamimidoyl-2,5-dihydro-pyrrol-3-yl)-propionylamino]-pentanoylamino}-3-hydroxy-3-thiophen-2-yl-propionic acid
40) {5-[2-Amino-3-(1-carbamimidoyl-2,5-dihydro-pyrrol-3-yl)-propionylamino]-pentanoylamino}-(3-methyl-benzo[b]thiophen-7-yl)-acetic acid
41) {5-[2-(2-Amino-3-hydroxy-butyrylamino)-3-(1-carbamimidoyl-2,5-dihydro-pyrrol-3-yl)-propionylamino]-pentanoylamino}-phenyl-acetic acid
42) 2-{5-[2-Amino-3-(1-carbamimidoyl-2,5-dihydro-pyrrol-3-yl)-propionylamino]-pentanoylamino}-3-(3,4-dihydroxy-phenyl)-3-hydroxy-propionic acid
43) {5-[2-(2-Amino-3-hydroxy-butyrylamino)-3-(1-carbamimidoyl-2,5-dihydro-pyrrol-3-yl)-propionylamino]-pentanoylamino}-(4-hydroxy-phenyl)-acetic acid
44) 2-{5-[2-Amino-3-(1-carbamimidoyl-2,5-dihydro-pyrrol-3-yl)-propionylamino]-pentanoylamino-3-phenyl-butyric acid
45) 2-{5-[2-(2-Amino-3-hydroxy-butyrylamino)-3-(1-carbamimidoyl-2,5-dihydro-pyrrol-3-yl)-propionylamino]-pentanoylamino}-3-(3,4-bis-benzyloxy-phenyl)-3-hydroxy-propionic acid
46) 2-{5-[2-Amino-3-(1-carbamimidoyl-2,5-dihydro-pyrrol-3-yl)-propionylamino]-pentanoylamino}-3-hydroxy-succinic acid
47) 2-({5-[2-(2-Amino-3-hydroxy-butyrylamino)-3-(1-carbamimidoyl-2,5-dihydro-pyrrol-3-yl)-propionylamino]-pentanoylamino}-carboxy-methyl)-benzoic acid
48) 5-[2-Amino-3-(1-carbamimidoyl-2,5-dihydro-pyrrol-3-yl)-propionylamino]-pentanoylamino}-(3-oxo-2,3-dihydro-isoxazol-5-yl)-acetic acid
49) {5-[2-(2-Amino-3-hydroxy-butyrylamino)-3-(1-carbamimidoyl-2,5-dihydro-pyrrol-3-yl)-propionylamino]-pentanoylamino}-cyclohexyl-acetic acid
50) {5-[2-Amino-3-(1-carbamimidoyl-2,5-dihydro-pyrrol-3-yl)-propionylamino]-pentanoylamino}-cyclohexa-1,4-dienyl-acetic acid
51) {5-[2-(2-Amino-3-hydroxy-butyrylamino)-3-(1-carbamimidoyl-2,5-dihydro-pyrrol-3-yl)-propionylamino]-pentanoylamino}-cyclohexa-1,5-dienyl-acetic acid
52) 2-{5-[2-Amino-3-(1-carbamimidoyl-2,5-dihydro-pyrrol-3-yl)-propionylamino]-pentanoylamino}-3-hydroxy-3-pyridin-3-yl-propionic acid
53) 2-{5-[2-(2-Amino-3-hydroxy-butyrylamino)-3-(1-carbamimidoyl-2,5-dihydro-pyrrol-3-yl)-propionylamino]-pentanoylamino}-3-hydroxy-3-pyridin-4-yl-propionic acid
54) 4-({5-[2-Amino-3-(1-carbamimidoyl-2,5-dihydro-pyrrol-3-yl)-propionylamino]-pentanoylamino)-carboxy-methyl)-2-hydroxy-benzoic acid
55) 4-({5-[2-(2-Amino-3-hydroxy-butyrylamino)-3-(1-carbamimidoyl-2,5-dihydro-pyrrol-3-yl)-propionylamino]-pentanoylamino}-carboxy-methyl)-benzoic acid
56) 2-{5-[2-Amino-3-(1-carbamimidoyl-2,5-dihydro-pyrrol-3-yl)-propionylamino]-pentanoylamino}-3-phenylsulfanyl-butyric acid
57) {5-[2-(2-Amino-3-hydroxy-butyrylamino)-3-(1-carbamimidoyl-2,5-dihydro-pyrrol-3-yl)-propionylamino]-pentanoylamino}-(tetrazol-5-yl)-acetic acid
58) {5-[2-Amino-3-(1-carbamimidoyl-2,5-dihydro-pyrrol-3-yl)-propionylamino]-pentanoylamino}-(indol-3-yl)-acetic acid
59) {5-[2-(2-Amino-3-hydroxy-butyrylamino)-3-(1-carbamimidoyl-2,5-dihydro-pyrrol-3-yl)-propionylamino]-pentanoylamino}-(3,4-dihydroxy-phenyl)-acetic acid
60) {5-[2-Amino-3-(1-carbamimidoyl-2,5-dihydro-pyrrol-3-yl)-propionylamino]-pentanoylamino}-(3,5-dihydroxy-phenyl)-acetic acid
61) 2-{4-[2-Amino-3-(1-carbamimidoyl-2,5-dihydro-pyrrol-3-yl)-propionylamino]-butyrylamino}-3-(indol-2-yl)-propionic acid
62) 2-{4-[2-(2-Amino-3-hydroxy-butyrylamino)-3-(1-carbamimidoyl-2,5-dihydro-pyrrol-3-yl)-propionylamino]-butyrylamino}-3-(7-methyl-indol-2-yl)-propionic acid
63) 2-{4-[2-Amino-3-(1-carbamimidoyl-2,5-dihydro-pyrrol-3-yl)-propionylamino]-butyrylamino}-3-benzo[b]thiophen-2-yl-propionic acid
64) 2-{4-[2-(2-Amino-3-hydroxy-butyrylamino)-3-(1-carbamimidoyl-2,5-dihydro-pyrrol-3-yl)-propionylamino]-butyrylamino}-3-(6-methyl-indol-2-yl)-propionic acid
65) 2-{4-[2-Amino-3-(1-carbamimidoyl-2,5-dihydro-pyrrol-3-yl)-propionylamino]-butyrylamino}-3-(6-hydroxy-indol-2-yl)-propionic acid
66) 2-{4-[2-(2-Amino-3-hydroxy-butyrylamino)-3-(1-carbamimidoyl-2,5-dihydro-pyrrol-3-yl)-propionylamino]-butyrylamino}-3-(3-methyl-indol-2-yl)-propionic acid
67) 2-{4-[2-Amino-3-(1-carbamimidoyl-2,5-dihydro-pyrrol-3-yl)-propionylamino]-butyrylamino}-3-(3-methyl-benzofuran-2-yl)-propionic acid
68) 2-{4-[2-(2-Amino-3-hydroxy-butyrylamino)-3-(1-carbamimidoyl-2,5-dihydro-pyrrol-3-yl)-propionylamino]-butyrylamino}-3-(3,4-dimethyl-benzofuran-2-yl)-propionic acid
69) 2-{4-[2-Amino-3-(1-carbamimidoyl-2,5-dihydro-pyrrol-3-yl)-propionylamino]-butyrylamino}-3-(3,5-dimethyl-benzofuran-2-yl)-propionic acid
70) 2-{4-[2-(2-Amino-3-hydroxy-butyrylamino)-3-(1-carbamimidoyl-2,5-dihydro-pyrrol-3-yl)-propionylamino]-butyrylamino}-3-(3,6-dimethyl-benzofuran-2-yl)-propionic acid
71) 2-{4-[2-Amino-3-(1-carbamimidoyl-2,5-dihydro-pyrrol-3-yl)-propionylamino]-butyrylamino}-3-(5-ethyl-3-methyl-benzofuran-2-yl)-propionic acid
72) 2-{4-[2-(2-Amino-3-hydroxy-butyrylamino)-3-(1-carbamimidoyl-2,5-dihydro-pyrrol-3-yl)-propionylamino]-butyrylamino}-3-hydroxy-3-(3-methyl-benzofuran-2-yl)-propionic acid
73) 2-{4-[2-Amino-3-(1-carbamimidoyl-2,5-dihydro-pyrrol-3-yl)-propionylamino]-butyrylamino}-3-(3,7-dimethyl-benzofuran-2-yl)-propionic acid
74) 2-{4-[2-(2-Amino-3-hydroxy-butyrylamino)-3-(1-carbamimidoyl-2,5-dihydro-pyrrol-3-yl)-

75) 2-{4-[2-Amino-3-(1-carbamimidoyl-2,5-dihydro-pyrrol-3-yl)-propionylamino]-butyrylamino}-3-(3,6-dimethyl-benzofuran-2-yl)-3-hydroxy-propionic acid
76) 2-{4-[2-(2-Amino-3-hydroxy-butyrylamino)-3-(1-carbamimidoyl-2,5-dihydro-pyrrol-3-yl)-propionylamino]-butyrylamino}-3-(3,5-dimethyl-benzofuran-2-yl)-3-hydroxy-propionic acid
77) 2-{4-[2-Amino-3-(1-carbamimidoyl-2,5-dihydro-pyrrol-3-yl)-propionylamino]-butyrylamino}-3-(3,4-dimethyl-benzofuran-2-yl)-3-hydroxy-propionic acid
78) 2-{4-[2-(2-Amino-3-hydroxy-butyrylamino)-3-(1-carbamimidoyl-2,5-dihydro-pyrrol-3-yl)-propionylamino]-butyrylamino}-3-(3,7-dimethyl-benzofuran-2-yl)-3-hydroxy-propionic acid
79) 2-{4-[2-Amino-3-(1-carbamimidoyl-2,5-dihydro-pyrrol-3-yl)-propionylamino]-butyrylamino}-3-(7-chloro-3-methyl-benzofuran-2-yl)-3-hydroxy-propionic acid
80) 2-{4-[2-(2-Amino-3-hydroxy-butyrylamino)-3-(1-carbamimidoyl-2,5-dihydro-pyrrol-3-yl)-propionylamino]-butyrylamino}-3-(5-ethyl-3-methyl-benzofuran-2-yl)-3-hydroxy-propionic acid
81) 2-{4-[2-Amino-3-(1-carbamimidoyl-2,5-dihydro-pyrrol-3-yl)-propionylamino]-butyrylamino}-3-(7-ethyl-3-methyl-benzofuran-2-yl)-3-hydroxy-propionic acid
82) 2-{4-[2-(2-Amino-3-hydroxy-butyrylamino)-3-(1-carbamimidoyl-2,5-dihydro-pyrrol-3-yl)-propionylamino]-butyrylamino}-3-furan-2-yl-propionic acid
83) 2-{4-[2-Amino-3-(1-carbamimidoyl-2,5-dihydro-pyrrol-3-yl)-propionylamino]-butyrylamino}-furan-2-yl-3-hydroxy-propionic acid
84) {4-[2-(2-Amino-3-hydroxy-butyrylamino)-3-(1-carbamimidoyl-2,5-dihydro-pyrrol-3-yl)-propionylamino]-butyrylamino}-thiophen-2-yl-acetic acid
85) 2-{4-[2-Amino-3-(1-carbamimidoyl-2,5-dihydro-pyrrol-3-yl)-propionylamino]-butyrylamino}-3-thiophen-2-yl-propionic acid
86) 2-{4-[2-(2-Amino-3-hydroxy-butyrylamino)-3-(1-carbamimidoyl-2,5-dihydro-pyrrol-3-yl)-propionylamino]-butyrylamino}-3-(pyrrol-2-yl)-propionic acid
87) 2-{4-[2-Amino-3-(1-carbamimidoyl-2,5-dihydro-pyrrol-3-yl)-propionylamino]-butyrylamino}-3-(5-methyl-thiophen-2-yl)-propionic acid
88) 2-{4-[2-(2-Amino-3-hydroxy-butyrylamino)-3-(1-carbamimidoyl-2,5-dihydro-pyrrol-3-yl)-propionylamino]-butyrylamino}-3-hydroxy-3-(5-methyl-thiophen-2-yl)-propionic acid
89) 2-{4-[2-Amino-3-(1-carbamimidoyl-2,5-dihydro-pyrrol-3-yl)-propionylamino]-butyrylamino}-3-(5-ethyl-thiophen-2-yl)-propionic acid
90) 2-{4-[2-(2-Amino-3-hydroxy-butyrylamino)-3-(1-carbamimidoyl-2,5-dihydro-pyrrol-3-yl)-propionylamino]-butyrylamino}-3-(5-propyl-thiophen-2-yl)-propionic acid
91) 2-{4-[2-Amino-3-(1-carbamimidoyl-2,5-dihydro-pyrrol-3-yl)-propionylamino]-butyrylamino}-3-(5-hydroxymethyl-furan-2-yl)-propionic acid
92) 5-(2-{4-[2-(2-Amino-3-hydroxy-butyrylamino)-3-(1-carbamimidoyl-2,5-dihydro-pyrrol-3-yl)-propionylamino]-butyrylamino}-2-carboxy-ethyl)-2-methyl-furan-3-carboxylic acid
93) 5-(2-{4-[2-Amino-3-(1-carbamimidoyl-2,5-dihydro-pyrrol-3-yl)-propionylamino]-butyrylamino}-2-carboxy-ethyl)-2-ethyl-furan-3-carboxylic acid
94) 5-(2-{4-[2-(2-Amino-3-hydroxy-butyrylamino)-3-(1-carbamimidoyl-2,5-dihydro-pyrrol-3-yl)-propionylamino]-butyrylamino}-2-carboxy-ethyl)-2-methyl-pyrrole-3-carboxylic acid ethyl ester
95) 5-(2-{4-[2-Amino-3-(1-carbamimidoyl-2,5-dihydro-pyrrol-3-yl)-propionylamino]-butyrylamino}-2-carboxy-ethyl)-2-propyl-furan-3-carboxylic acid
96) 3-(5-Acetylimino-4,5-dihydro-thiophen-2-yl)-2-{4-[2-(2-amino-3-hydroxy-butyrylamino)-3-(1-carbamimidoyl-2,5-dihydro-pyrrol-3-yl)-propionylamino]-butyrylamino}-3-hydroxy-propionic acid
97) 5-(2-{4-[2-Amino-3-(1-carbamimidoyl-2,5-dihydro-pyrrol-3-yl)-propionylamino]-butyrylamino}-2-carboxy-ethyl)-2-isobutyl-furan-3-carboxylic acid
98) 2-{4-[2-(2-Amino-3-hydroxy-butyrylamino)-3-(1-carbamimidoyl-2,5-dihydro-pyrrol-3-yl)-propionylamino]-butyrylamino}-3-cyclopent-1-enyl-propionic acid
99) 2-{4-[2-Amino-3-(1-carbamimidoyl-2,5-dihydro-pyrrol-3-yl)-propionylamino]-butyrylamino}-3-hydroxy-3-thiophen-2-yl-propionic acid
100) {4-[2-(2-Amino-3-hydroxy-butyrylamino)-3-(1-carbamimidoyl-2,5-dihydro-pyrrol-3-yl)-propionylamino]-butyrylamino}-(3-methyl-benzo[b]thiophen-7-yl)-acetic acid
101) {4-[2-Amino-3-(1-carbamimidoyl-2,5-dihydro-pyrrol-3-yl)-propionylamino]-butyrylamino}-phenyl-acetic acid
102) 2-{4-[2-(2-Amino-3-hydroxy-butyrylamino)-3-(1-carbamimidoyl-2,5-dihydro-pyrrol-3-yl)-propionylamino]-butyrylamino}-3-(3,4-dihydroxy-phenyl)-3-hydroxy-propionic acid
103) {4-[2-Amino-3-(1-carbamimidoyl-2,5-dihydro-pyrrol-3-yl)-propionylamino]-butyrylamino}-(4-hydroxy-phenyl)-acetic acid
104) 2-{4-[2-(2-Amino-3-hydroxy-butyrylamino)-3-(1-carbamimidoyl-2,5-dihydro-pyrrol-3-yl)-propionylamino]-butyrylamino}-3-phenyl-butyric acid
105) 2-{4-[2-Amino-3-(1-carbamimidoyl-2,5-dihydro-pyrrol3-yl)-propionylamino]-butyrylamino}-3-(3,4-bis-benzyloxy-phenyl)-3-hydroxy-propionic acid
106) 2-{4-[2-(2-Amino-3-hydroxy-butyrylamino)-3-(1-carbamimidoyl-2,5-dihydro-pyrrol-3-yl)-propionylamino]-butyrylamino}-3-hydroxy-succinic acid
107) 2-({4-[2-Amino-3-(1-carbamimidoyl-2,5-dihydro-pyrrol-3-yl)-propionylamino]-butyrylamino}-carboxy-methyl)-benzoic acid
108) 5-[2-(2-Amino-3-hydroxy-butyrylamino)-3-(1-carbamimidoyl-2,5-dihydro-pyrrol-3-yl)-propionylamino]-butyrylamino}-(3-oxo-2,3-dihydro-isoxazol-5-yl)-acetic acid
109) {4-[2-Amino-3-(1-carbamimidoyl-2,5-dihydro-pyrrol-3-yl)-propionylamino]-butyrylamino}-cyclohexyl-acetic acid
110) {4-[2-(2-Amino-3-hydroxy-butyrylamino)-3-(1-carbamimidoyl-2,5-dihydro-pyrrol-3-yl)-propionylamino]-butyrylamino}-cyclohexa-1,4-dienyl-acetic acid
111) {4-[2-Amino-3-(1-carbamimidoyl-2,5-dihydro-pyrrol-3-yl)-propionylamino]-butyrylamino}-cyclohexa-1,5-dienyl-acetic acid
112) 2-{4-[2-(2-Amino-3-hydroxy-butyrylamino)-3-(1-carbamimidoyl-2,5-dihydro-pyrrol-3-yl)-propionylamino]-butyrylamino}-3-hydroxy-3-pyridin-3-yl-propionic acid
113) 2-{4-[2-Amino-3-(1-carbamimidoyl-2,5-dihydro-pyrrol-3-yl)-propionylamino]-butyrylamino}-3-hydroxy-3-pyridin4-yl-propionic acid 114) 4-({4-[2-(2-Amino-3-hydroxy-butyrylamino)-3-(1-carbamimidoyl-2,5-dihydro-pyrrol-3-yl)-propionylamino]-butyrylamino}-carboxy-methyl)-2-hydroxy-benzoic acid
115) 4-({4-[2-Amino-3-(1-carbamimidoyl-2,5-dihydro-pyrrol-3-yl)-propionylamino]-butyrylamino}-carboxy-methyl)-benzoic acid
116) 2-{4-[2-(2-Amino-3-hydroxy-butyrylamino)-3-(1-carbamimidoyl-2,5-dihydro-pyrrol-3-yl)-propionylamino]-butyrylamino}-3-phenylsulfanyl-butyric acid
117) {4-[2-Amino-3-(1-carbamimidoyl-2,5-dihydro-pyrrol-3-yl)-propionylamino]-butyrylamino}-(tetrazol-5-yl)-acetic acid
118) {4-[2-(2-Amino-3-hydroxy-butyrylamino)-3-(1-carbamimidoyl-2,5-dihydro-pyrrol-3-yl)-propionylamino]-butyrylamino}-(indol-3-yl)-acetic acid
119) {4-[2-Amino-3-(1-carbamimidoyl-2,5-dihydro-pyrrol-3-yl)-propionylamino]-butyrylamino}-(3,4-dihydroxy-phenyl)-acetic acid
120) {4-[2-(2-Amino-3-hydroxy-butyrylamino)-3-(1-carbamimidoyl-2,5-dihydro-pyrrol-3-yl)-propionylamino]-butyrylamino}-(3,5-dihydroxy-phenyl)-acetic acid
121) 2-{3-[2-(2-Amino-3-hydroxy-butyrylamino)-3-(1-carbamimidoyl-2,5-dihydro-pyrrol-3-yl)-propionylamino]-propionylamino}-3-(indol-2-yl)-propionic acid
122) 2-{6-[2-Amino-3-(1-carbamimidoyl-2,5-dihydro-pyrrol-3-yl)-propionylamino]-hexanoylamino}-3-(7-methyl-indol-2-yl)-propionic acid
123) 2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}-propionylamino)-3-benzo[b]thiophen-2-yl-propionic acid
124) 2-{3-[2-Amino-3-(1-carbamimidoyl-2,5-dihydro-pyrrol-3-yl)-propionylamino]-propionylamino}-3-(6-methyl-indol-2-yl)-propionic acid
125) 2-{6-[2-(2-Amino-3-hydroxy-butyrylamino)-3-(1-carbamimidoyl-2,5-dihydro-pyrrol-3-yl)-propionylamino]-hexanoylamino}-3-(6-hydroxy-indol-2-yl)-propionic acid
126) 2-(2-{2-[2-Amino-3-(1-carbamimidoyl-2,5-dihydro-pyrrol-3-yl)-propionylamino]-3-hydroxy-propionylamino}-propionylamino)-3-(3-methyl-indol-2-yl)-propionic acid
127) 2-{3-[2-(2-Amino-3-hydroxy-butyrylamino)-3-(1-carbamimidoyl-2,5-dihydro-pyrrol-3-yl)-propionylamino]-propionylamino}-3-(3-methyl-benzofuran-2-yl)-propionic acid
128) 2-(2-{2-[2-Amino-3-(1-carbamimidoyl-2,5-dihydro-pyrrol-3-yl)-propionylamino]-3-hydroxy-propionylamino}-propionylamino)-3-(3,4-dimethyl-benzofuran-2-yl)-propionic acid
129) 2-{6-[2-(2-Amino-3-hydroxy-butyrylamino)-3-(1-carbamimidoyl-2,5-dihydro-pyrrol-3-yl)-propionylamino]-hexanoylamino}-3-(3,5-dimethyl-benzofuran-2-yl)-propionic acid
130) 2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}-propionylamino)-3-(5-ethyl-3-methyl-benzofuran-2-yl)-propionic acid
131) 2-{3-[2-Amino-3-(1-carbamimidoyl-2,5-dihydro-pyrrol-3-yl)-propionylamino]-propionylamino}-3-hydroxy-3-(3-methyl-benzofuran-2-yl)-propionic acid
132) 2-(2-{2-[2-(2-Amino-3-hydroxy-butyrylamino)-3-(1-carbamimidoyl-2,5-dihydro-pyrrol-3-yl)-propionylamino]-3hydroxy-propionylamino}-propionylamino)3-(3,7-dimethyl-benzofuran-2-yl)-propionic acid
133) 2-{6-[2-Amino-3-(1-carbamimidoyl-2,5-dihydro-pyrrol-3-yl)-propionylamino]-hexanoylamino}-3-(7-ethyl-3-methyl-benzofuran-2-yl)-propionic acid
134) 2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}-propionylamino)-3-(3,6-dimethyl-benzofuran-2-yl)-3-hydroxy-propionic acid
135) 2-{3-[2-Amino-3-(1-carbamimidoyl-2,5-dihydro-pyrrol-3-yl)-propionylamino]-propionylamino}-3-(3,5-dimethyl-benzofuran-2-yl)-3-hydroxy-propionic acid
136) 2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}-propionylamino)-3-(3,4-dimethyl-benzofuran-2-yl)-3-hydroxy-propionic acid
137) 2-{6-[2-Amino-3-(1-carbamimidoyl-2,5-dihydro-pyrrol-3-yl)-propionylamino]-hexanoylamino}-3-(3,7-dimethyl-benzofuran-2-yl)-3-hydroxy-propionic acid
138) 2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}-propionylamino)-3-(7-chloro-3-methyl-benzofuran-2-yl)-3-hydroxy-propionic acid
139) 2-{3-[2-Amino-3-(1-carbamimidoyl-2,5-dihydro-pyrrol-3-yl)-propionylamino]-propionylamino}-3-(5-ethyl-3-methyl-benzofuran-2-yl)-3-hydroxy-propionic acid
140) 2-{6-[2-(2-Amino-3-hydroxy-butyrylamino)-3-(1-carbamimidoyl-2,5-dihydro-pyrrol-3-yl)-propionylamino]-hexanoylamino}-3-(7-ethyl-3-methyl-benzofuran-2-yl)-3-hydroxy-propionic acid
141) 2-{6-[2-Amino-3-(1-carbamimidoyl-2,5-dihydro-pyrrol-3-yl)-propionylamino]-hexanoylamino}-3-furan-2-yl-propionic acid
142) 2-{3-[2-(2-Amino-3-hydroxy-butyrylamino)-3-(1-carbamimidoyl-2,5-dihydro-pyrrol-3-yl)-propionylamino]-propionylamino}-3-furan-2-yl-3-hydroxy-propionic acid
143) {3-[2-Amino-3-(1-carbamimidoyl-2,5-dihydro-pyrrol-3-yl)-propionylamino]-propionylamino}-thiophen-2-yl-acetic acid
144) 2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}-propionylamino)-3-thiophen-2-yl-propionic acid
145) 2-{6-[2-Amino-3-(1-carbamimidoyl-2,5-dihydro-pyrrol-3-yl)-propionylamino]-hexanoylamino}-3-(pyrrol-2-yl)-propionic acid
146) 2-{3-[2-(2-Amino-3-hydroxy-butyrylamino)-3-(1-carbamimidoyl-2,5-dihydro-pyrrol-3-yl)-propionylamino]-propionylamino}-3-(5-methyl-thiophen-2-yl)-propionic acid
147) 2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}-propionylamino)-3-(5-ethyl-thiophen-2-yl)-propionic acid
148) 2-{3-[2-Amino-3-(1-carbamimidoyl-2,5-dihydro-pyrrol-3-yl)-propionylamino]-propionylamino}-3-(5-propyl-thiophen-2-yl)-propionic acid
149) 2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}- propionylamino)-3-(5-hydroxymethyl-furan-2-yl)-propionic acid
150) 5-(2-{6-[2-Amino-3-(1-carbamimidoyl-2,5-dihydro-pyrrol-3-yl)-propionylamino]-hexanoylamino}-2-carboxy-ethyl)-2-methyl-furan-3-carboxylic acid
151) 5-(2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}-propionylamino)-2-carboxy-ethyl)-2-ethyl-furan-3-carboxylic acid
152) 5-(2-{3-[2-Amino-3-(1-carbamimidoyl-2,5-dihydro-pyrrol-3-yl)-propionylamino]-propionylamino}-2-carboxy-ethyl)-2-methyl-pyrrole-3-carboxylic acid ethyl ester
153) 5-(2-{6-[2-(2-Amino-3-hydroxy-butyrylamino)-3-(1-carbamimidoyl-2,5-dihydro-pyrrol-3-yl)-propionylamino]-hexanoylamino}-2-carboxy-ethyl)-2-propyl-furan-3-carboxylic acid
154) 5-(2-{3-[2-(2-Amino-3-hydroxy-butyrylamino)-3-(1-carbamimidoyl-2,5-dihydro-pyrrol-3-yl)-propionylamino]-propionylamino}-carboxy-ethyl)-2-isobutyl-furan-3-carboxylic acid
155) (2-{2-[2-Amino-3-(1-carbamimidoyl-2,5-dihydro-pyrrol-3-yl)-propionylamino]-3-hydroxy-propionylamino}-propionylamino)-3-cyclopent-1-enyl-propionic acid
156) 2-{3-[2-(2-Amino-3-hydroxy-butyrylamino)-3-(1-carbamimidoyl-2,5-dihydro-pyrrol-3-yl)-propionylamino]-propionylamino}-3-hydroxy-3-thiophen-2-yl-propionic acid
157) 2-{6-[2-Amino-3-(1-carbamimidoyl-2,5-dihydro-pyrrol-3-yl)-propionylamino]-hexanoylamino}-3-(3,4-dihydroxy-phenyl)-3-hydroxy-propionic acid
158) 2-{3-[2-Amino-3-(1-carbamimidoyl-2,5-dihydro-pyrrol-3-yl)-propionylamino]-propionylamino}-3-phenyl-butyric acid
159) 2-(2-{2-[2-(2-Amino-3-hydroxy-butyrylamino)-3-(1-carbamimidoyl-2,5-dihydro-pyrrol-3-yl)-propionylamino]-3-hydroxy-propionylamino}-propionylamino)-3-(3,4-bis-benzyloxy-phenyl)-3-hydroxy-propionic acid
160) 2-{6-[2-Amino-3-(1-carbamimidoyl-2,5-dihydro-pyrrol-3-yl)-propionylamino]-hexanoylamino}-3-hydroxy-succinic acid
161) {3-[2-Amino-3-(1-carbamimidoyl-2,5-dihydro-pyrrol-3-yl)-propionylamino]-propionylamino}-cyclohexa-1,4-dienyl-acetic acid
162) 2-{3-[2-Amino-3-(1-carbamimidoyl-2,5-dihydro-pyrrol-3-yl)-propionylamino]-propionylamino}-3-hydroxy-3-pyridin-3-yl-propionic acid
163) 4-({6-[2-Amino-3-(1-carbamimidoyl-2,5-dihydro-pyrrol-3-yl)-propionylamino]-hexanoylamino}-carboxy-methyl)-2-hydroxy-benzoic acid
164) 2-{3-[2-Amino-3-(1-carbamimidoyl-2,5-dihydro-pyrrol-3-yl)-propionylamino]-propionylamino}-3-phenylsulfanyl-butyric acid
165) {6-[2-Amino-3-(1-carbamimidoyl-2,5-dihydro-pyrrol-3-yl)-propionylamino]-hexanoylamino}-(indol-3-yl)-acetic acid
166) {3-[2-Amino-3-(1-carbamimidoyl-2,5-dihydro-pyrrol-3-yl)-propionylamino]-propionylamino}-(3,5-dihydroxy-phenyl)-acetic acid
167) (2-{2-[2-(2-Amino-3-hydroxy-butyrylamino)-3-(1-carbamimidoyl-2,5-dihydro-pyrrol-3-yl)-propionylamino]-propionylamino}-propionylamino)-3-(6-hydroxy-indol-2-yl)-propionic acid
168) (2-{2-[2-Amino-3-(1-carbamimidoyl-2,5-dihydro-pyrrol-3-yl)-propionylamino]-propionylamino}-propionylamino)-3-(3,6-dimethyl-benzofuran-2-yl)-propionic acid
169) 2-(2-{2-[2-(2-Amino-3-hydroxy-butyrylamino)-3-(1-carbamimidoyl-2,5-dihydro-pyrrol-3-yl)-propionylamino]-propionylamino}-propionylamino)-3-(3,4-dimethyl-benzofuran-2-yl)-3-hydroxy-propionic acid
170) 2-(2-{2-[2-(2-Amino-3-hydroxy-butyrylamino)-3-(1-carbamimidoyl-2,5-dihydro-pyrrol-3-yl)-propionylamino]-propionylamino}-propionylamino )-3-(7-ethyl-3-methyl-benzofuran-2-yl)-3-hydroxy-propionic acid
171) 2-(2-{2-[2-(2-Amino-3-hydroxy-butyrylamino)-3-(1-carbamimidoyl-2,5-dihydro-pyrrol-3-yl)-propionylamino]-propionylamino}-propionylamino)-3-thiophen-2-yl-propionic acid
172) 2-(2-{2-[2-(2-Amino-3-hydroxy-butyrylamino)-3-(1-carbamimidoyl-2,5-dihydro-pyrrol-3-yl)-propionylamino]-propionylamino}-propionylamino)-3-(5-methyl-thiophen-2-yl)-propionic acid
173) 2-(2-{2-[2-(2-Amino-3-hydroxy-butyrylamino)-3-(1-carbamimidoyl-2,5-dihydro-pyrrol-3-yl)-propionylamino]-propionylamino}-propionylamino)-3-(5-hydroxymethyl-furan-2-yl)-propionic acid
174) 3-(5-Acetylimino-4,5-dihydro-thiophen-2-yl)-(2-{2-[-Amino-3-(1-carbamimidoyl-2,5-dihydro-pyrrol-3-yl)-propionylamino]-propionylamino}-propionylamino)-3-hydroxy-propionic acid
175) (2-{2-[2-(2-Amino-3-hydroxy-butyrylamino)-3-(1-carbamimidoyl-2,5-dihydro-pyrrol-3-yl)-propionylamino]-propionylamino}-propionylamino)-phenyl-acetic acid
176) (2-{2-[2-Amino-3-(1-carbamimidoyl-2,5-dihydro-pyrrol-3-yl)-propionylamino]-propionylamino}-propionylamino)-3-(3,4-dihydroxy-phenyl)-3-hydroxy-propionic acid
177) 2-(2-{2-[2-(2-Amino-3-hydroxy-butylamino)-3-(1-carbamimidoyl-2,5-dihydro-pyrrol-3-yl)-propionylamino]-propionylamino}-propionylamino)-3-(3,4-bis-benzyloxy-phenyl)-3-hydroxy-propionic acid
178) 2-((2-{2-[2-(2-Amino-3-hydroxy-butyrylamino)-3-(1-carbamimidoyl-2,5-dihydro-pyrrol-3-yl)-propionylamino]-propionylamino}-propionylamino)-carboxy-methyl)-benzoic acid
179) 2-(2-{2-[2-(2-Amino-3-hydroxy-butyrylamino)-3-(1-carbamimidoyl-2,5-dihydro-pyrrol-3-yl)-propionylamino]-propionylamino}-propionylamino)-3-hydroxy-3-pyridin-4-yl-propionic acid
180) (2-{2-[2-(2-Amino-3-hydroxy-butyrylamino)-3-(1-carbamimidoyl-2,5-dihydro-pyrrol-3-yl)-propionylamino]-propionylamino}-propionylamino)-(tetrazol-5-yl)-acetic acid
181) (2-{2-[2-(2-Amino-3-hydroxy-butyrylamino)-3-(1-carbamimidoyl-2,5-dihydro-pyrrol-3-yl)-propionylamino]-propionylamino}-propionylamino)-(3,4-dihydroxy-phenyl)-acetic acid The following examples exemplify variants for the synthesis of the compounds of the invention. The structure of the compounds was obtained by $^1$H—, $^{13}$C-NMR-s spectroscopy and optionally by mass-spectroscopy. The purity of the substances was obtained by C, H, N analyses and by chromatography.

EXAMPLE 1

(±)-3-(2-tert.-Butoxycarbonyl-amino-2-hydroxycarbonyl)-ethyl-2,5-dihydropyrrole-1-(N,N'-di-tert.-butoxycarbonyl) carboxamidine [Boc-Ada(Boc)$_2$OH]

a) 4-Oxo-pyrrolidine-1,3-dicarboxylic acid 1-tert. butylester 3-ethylester (J. Cooper et al. J. Chem.Soc.Perkin Trans. 1, 1993, 1313–1318)

To a refluxing suspension of 1.58 g (66 mmol) sodium hydride in 100 ml THF was added dropwise a solution of 12.79 g (60 mmol) N-tert-butyloxycarbonyl-glycine ethyl ester and 7.15 g (66 mmol) ethyl acrylate in 100 ml THF. After the addition was complete the mixture was heated to reflux for additional 2 h. The clear solution was cooled to room temperature, poured on 100 ml ether/100 ml water and acidified under vigorous stirring with 1N hydrochloric acid against methyl orange. The layers were separated and the aqueous layer was extracted three times with ether. The combined organic layers were washed with sat. sodium bicarbonate and brine, dried over MgSO$_4$ and evaporated. Short-path distillation of the residue gave 10.92 g (71%) 4-oxo-pyrrolidine-1,3-dicarboxylic acid 1-tert. butylester 3-ethylester as a colorless oil, b.p. 119–122° C. (0.2 mbar), which solidified on prolonged standing in the freezer.

GC/MS (HP 5890 II/HP 5972; column: HP 5, 30 m×25 mm×0.25 μm film thickness, carrier gas: helium; temperature gradient: 50° C., 3 min, then with 20° C./min to 250° C.) $t_R$=9.68 min m/z [%]=185 (2), 130 (10), 112 (18), 85 (6), 57 (100).

b) 4-Hydroxy-pyrrolidine-1,3-dicarboxylic acid 1-tert.-butylester 3-ethylester To a solution of 5.15 g (20 mmol) 4-oxo-pyrrolidine-1,3-dicarboxylic acid 1-tert. butylester 3-ethylester in 30 ml methanol was added 1.88 g (30 mmol) sodium cyanoborohydride and a small amount of methylorange. With stirring the pH was adjusted to 3 by dropwise addition of 1N hydrochloric acid (color change from yellow to orange). After no more acid was consumed the mixture was stirred for one hour. The solvent was evaporated in vacuo and the residue was partitioned between ethyl acetate and water. The organic layer was washed twice with water, then with brine, dried over magnesium sulfate and evaporated. The residual yellow oil was used in the next step without any further purification.

GC/MS (HP 5890 II/HP 5972; column: HP 5, 30 m×25 mm×0.25 μm film thickness, carrier gas: helium, temperature gradient: 50° C., 3 min; then with 20° C./min to 250° C.;) $t_R$=12.44 min (no separation of diastereomers) m/z [%]=259 (M$^+$,0.3), 241 (0.7), 202(5), 186 (7), 158 (10), 112 (14), 68 (31), 57 (100).

c) 4-Benzoyloxy-pyrrolidine-1,3-dicarboxylic acid 1-tert.-butylester3-ethylester To an ice-cooled solution of the crude 4-hydroxy-pyrrolidine-1,3-dicarboxylic acid 1-tert.-butylester 3-ethylester from the reduction described above and 244 mg (2 mmol) DMAP in 40 ml pyridine were added dropwise 3.51 g (25 mmol) benzoyl chloride. After the addition was complete, the ice bath was removed and the mixture was stirred at room temperature for 2 h. The mixture was diluted with ethyl acetate an poured on ice. The organic layer was separated. washed with water, sat. CuSO$_4$, water and brine, dried over MgSO$_4$ and evaporated. The residual yellow oil was used in the next step without further purification.

GC/MS (HP 5890 II/HP 5972, column: HP 5, 30 m×25 mm×0.25 μm film thickness, carrier gas: helium, temperature gradient: 50° C., 3 min. then with 20° C./min to 250° C.) $t_R$=17.28 and 17.38 min (1:1-mixture of cis/trans-isomers) m/z [%]=318 (0.1), 290 (5), 262 (2), 241 (2), 185 (29), 141 (10), 112 (23), 105 (53), 77 (27), 68 (100), 57 (97).

d) 2,5-Dihydro-pyrrole-1,3-dicarboxylic acid 1-tert.-butylester 3-ethyl ester To a solution of the crude 4-benzoyloxy-pyrrolidine-1,3-dicarboxylic acid 1-tert.-butylester 3-ethylester from the benzoylation described above in 75 ml dry toluene was added 4.11 g (27 mmol) DBU. The dark, heterogeneous mixture was stirred at room temperature for 16 h. After this time no starting material was detectable by TLC and GC analysis. The mixture was filtered through a short column of silica (elution with petrolether/ethyl acetate 1:1) and evaporated. Bulb-to-bulb distillation of the residual slightly yellow oil gave 4.16 g (86%) 2,5-dihydro-pyrrole-1,3-dicarboxylic acid 1-tert.-butylester 3-ethyl ester as a colorless oil b.p. 110° C./0.2 mbar, which slowly solidified to a waxy mass on standing in the freezer.

GC/MS (HP 5890 II/HP 5972, column: HP 5, 30 m×25 mm×0.25 μm film thickness, carrier gas: helium: temperature gradient: 50° C., 3 min: then with 20° C./min to 250° C.) $t_R$=11.94 min m/z [%]=241 (M$^+$,1.4), 196 (0.4), 185 (11), 168 (11), 140 (14), 112 (17), 68 (24) 57 (100).

$^1$H-NMR (CDCl$_3$, 300 MHz) d=1.27 (t, J=7.1 Hz, 3H, OCH$_2$C<u>H</u>$_3$), 1.43, 1.44 [2s, 9H, C(CH$_3$)$_3$]$^\#$, 4.25 (d, J=7.1 Hz, 2H, OC<u>H</u>$_2$CH$_3$), 4.15–4.27 (br. m, 4H, 2-H, 5-H), 6.66–6.71 (m, 1H, 4-H), ppm. Double set of signals due to hindered rotation.

$^{13}$C-NMR (CDCl$_3$, 75 MHz) d=14.16, 14.20 (q, —CH$_2$—<u>C</u>$_3$)*, 28.45 [q, —C(<u>C</u>H$_3$)$_3$], 51.76, 51.99, 53.62, 53.84 (4t, C-2, C-5)*, 60.69 (t, —<u>C</u>H$_2$—CH$_3$), 79.84 [s, —<u>C</u>(CH$_3$)$_3$], 132.29 (s, C-3), 136.44, 136.55 (2d, C-4)*, 153.86, 154.08 (2s, —NCOO—)*, 162.75 (s, COOEt) ppm.

e) 3-Hydroxymethyl-2,5-dihydro-pyrrole-1-carboxylic acid tert.-butylester

To a solution of 5.43 g (22.5 mmol) 2,5-dihydro-pyrrole-1,3-dicarboxylic acid 1-tert.-butylester 3-ethyl ester in 50 ml THF, cooled to −78° C. was dropwise added 50 ml of a 1N DIBAL-H solution in hexane. The mixture was allowed to warm to room temperature overnight. As TLC analysis indicated complete consumption of starting material, the mixture was cooled in an ice bath and 1.90 g water were cautiously added, followed by 1.90 g 15% aqueous NaOH and 5.70 g water. The white precipitate was filtered off, washed thoroughly with ether and the combined filtrates were evaporated. Bulb-to-bulb distillation of the residual pale yellow oil gave 4.13 g (93%) 3-hydroxymethyl-2,5-dihydro-pyrrole-1-carboxylic acid tert.-butylester as a colorless oil, b.p. 130° C. (0.2 mbar).

GC/MS (HP 5890 II/HP 5972; column: HP 5, 30 m×25 mm×0.25 μm film thickness, carrier gas: helium; temperature gradient: 50° C., 3 min, then with 20° C./min to 250° C.) $t_R$=11.34 min m/z [%]=199 (M$^+$, 1), 143 (10), 142 (13), 126 (13), 112 (12), 80 (10), 68 (45), 57 (100).

$^1$H-NMR (CDCl$_3$, 300 MHz) d=1.44 (s, 9H, t-Bu), 4.09 (br. m, 4H, 2-H, 4-H), 4.18 (br. s, 2H, CH$_2$OH), 5.63 (br. d, 1H, 4-H) ppm.

$^{13}$C-NMR (CDCl$_3$, 75 MHz) d=28.5 [q, C(<u>C</u>H$_3$)$_3$], 52.8, 53.0, 53.2, 53.3 (4t, C-2, C-5)#, 57.7, 59.8 (2d, CH$_2$OH), 79.5 [s, <u>C</u>(CH$_3$)$_3$], 120.0, 120.3 (2d, C-4), 139.6 (s, C-3), 154.4 (s, COOtBu) ppm. Double set of signals due to hindered rotation.

f) 3-Acetoxymethyl-2,5-dihydro-pyrrole-1-carboxylic acid tert.-butylester

To an ice-cooled solution of 4.13 g (20.7 mmol) 3-hydroxymethyl-2,5-dihydro-pyrrole-1-carboxylic acid tert.-butylester and 244 mg (2 mmol) DMAP in 50 ml pyridine was added 3.06 g (30 mmol) acetic anhydride. The mixture was stirred for 30 min at 0° C., then for additional 60 min at room temperature. The mixture was poured on ice and extracted twice with ether. The combined organic layers were evaporated in vacuo, dissolved in ether, washed with sat. $CuSO_4$, water and brine and dried over $MgSO_4$. Evaporation and bulb-to-bulb distillation gave 4.82 g (97%) 3-acetoxymethyl-2,5-dihydro-pyrrole-1-carboxylic acid tert.-butylester as a colorless oil, b.p. 105° C. (0.2 mbar).

GC/MS (HP 5890 II/HP 5972; column: HP 5, 30 m×25 mm×0.25 μm film thickness, carrier gas: helium; temperature gradient: 50° C., 3 min: then with 20° C./min to 250° C.) $t_R$=11.87 min m/z[%]=241 ($M^+$, 0.2), 226 (0.1), 185 (5), 166 (5), 125 (18), 108 (3), 81 (13), 80 (23), 57 (100).

$^1$H-NMR ($CDCl_3$, 300 MHz) d=1.43, 1.44 [2s, 9H, $C(CH_3)_3$]*, 2.04, 2.06 (2s, 3H, OOCCH$_3$)*, 4.05–4.12 (br. m, 4H, 2-H, 5-H), 4.61 (br. d, J=5.7 Hz, 2H, CH$_2$O), 5.66–5.73 (br. m, 1H, 4-H) ppm.

$^{13}$C-NMR ($CDCl_3$, 75 MHz) d=20.7 (q, OOCCH$_3$), 28.4 [q, C(CH$_3$)$_3$], 53.0, 53.2, 53.3 (3t, 2-C, 5-C)*, 60.8 (t, CH$_2$OAc), 79.5 [s, C(CH$_3$)$_3$], 123.4, 123.8 (2d, C-4)*, 134.5, 134,6 (2s, C-3), 154.1 (s, NCOO), 170.5 (s, OOCCH$_3$) ppm.

g) 3-Acetoxymethyl-2,5-dihydro-pyrrole-1-(N,N'-di-tert.-butoxycarbonyl) carboxamidine To an ice-cooled solution of 1.21 g (5 mmol) 3-acetoxymethyl-2,5-dihydro-pyrrole-1-carboxylic acid tert.-butylester from example 3f) in 10 ml dry dioxane was added 10 ml 4N hydrogen chloride in dioxane. The mixture was stirred at 0° C. for 16 h. The mixture was evaporated to dryness without heating and then evacuated in high vacuum for several hours. The dark residue was suspended in 20 ml dry acetonitrile and 776 mg (6 mmol) ethyl diisopropylamine, followed by 1.71 g (5.5 mmol) N,N'-bis-tert.-butyloxycarbonyl-1H-pyrazole-1-carboxamidine were added. The mixture was stirred for 2 h at room temperature and then evaporated and purified by flash chromatography (petrol ether/ethyl acetate 3:1 to 2:1) to yield 1.87 g (97%) of 3-acetoxymethyl-2,5-dihydro-pyrrole-1-(N,N'-di-tert.-butoxycarbonyl) carboxamidine as a colorless, sticky solid.

$^1$H-NMR ($CDCl_3$, 300 MHz) d=1.45 (s, 18H, 2 t-Bu), 2.03 (s, 3H OAc), 4.38 (br. m, 4H, 2-H, 5-H), 4.61 (s, 2H CH$_2$OAc), 5.72 (br. m, 1H, 4-H), 10.22 (br. s, 1H, NH) ppm.

$^{13}$C-NMR ($CDCl_3$, 75 MHz) d=20.4 (q, OOCCH$_3$), 27.7, 27.9 [2q, C(CH$_3$)$_3$], 55.0 (br. t, C-2, C-5), 60.2 (t, CH$_2$OAc), 79.3, 81.8 [2 br. s, C(CH$_3$)$_3$], 122.4 (d, C-4), 133.5 (s, C-3), 150 (br. s, NCOO), 153.9 (s, NC=N), 162 (br. s, NCOO), 170.2 (s, OOCH$_2$CH$_3$) ppm.

h) 3(2-Benzhydrilideneamino-2-ethoxycarbonyl-ethyl)-2,5-dihydropyrrole-1-(N,N'-di-tert.-butoxycarbonyl) carboxamidine To a solution of lithium hexamethyldisilazide, freshly prepared at 0° C. from 710 mg (4.4 mmol) hexamethyldisilazane in 8 ml THF and 1.92 g (4.4 mmol) n-Butyl-lithium, (2.29 mmol/g in hexanes) and cooled to −78° C. was added a solution of 1.069 g (4 mmol) ethyl N-(diphenylmethylene)-glycinate in 8 ml THF. The orange enolate solution was stirred for 30 min at −78° C., then a solution of 1.039 g (3.7 mmol) 3-acetoxymethyl-2,5-dihydro-pyrrole-1-(N,N'-di-tert.-butoxycarbonyl) carboxamidine and 426 mg (0.4 mmol) Pd(PPh$_3$)$_4$ in 12 ml THF was added dropwise. The reaction mixture was allowed to warm to room temperature over 2 h and was stirred for additional 12 h. The mixture was diluted with ether and quenched by addition of sat. NaHCO$_3$. The organic layer was washed with sat. NaHCO$_3$ and brine, dried over MsSO$_4$ and evaporated. Purification by flash chromatography (ethyl acetate/petrol ether 1:5+1% triethylamine) gave 1.03 g (47 %) of 3-(2-benzhydrylideneamino-2-ethoxycarbonyl-ethyl)-2,5-dihydropyrrole-1-(N,N'-di-tert.-butoxycarbonyl) carboxamidine as a colorless, amorphous solid.

$^1$NMR ($CDCl_3$, 300 MHz) d=1.23 (t, J=7.1 Hz, 3H, OCH$_2$CH$_3$), 1.46 [br. s, 18H, C(CH$_3$)$_3$], 2.68 (br. m, 2H, 3-CH$_2$—), 3.96 (br. m, 1H, CH—N), 4.15 (q, J=7.1 Hz, 2H, OCH$_2$CH$_3$), 4.16–4.29 (br. m, 4H, 2-H, 5-H), 5.41 (br. m, 1H, 4-H), 7.07–7.60 (m, 10 H, Ar—H) ppm.

$^{13}$C-NMR ($CDCl_3$, 75 MHz) d=13.9 (q, OCH$_2$CH$_3$), 28.0 [q, C(CH$_3$)$_3$], 32.5 (t, 3-CH$_2$), 55.2, 56.9 (2t, C-2, C-5), 60.9 (t, OCH$_2$CH$_3$), 63.6 (d, CH—NH$_2$), 79, 81.6 [2 br. s, C(CH$_3$)$_3$], 120.7 (d, C-4), 127.5, 127.8, 128.4, 128.5, 128.6, 130.2 (6d, Ar—CH), 134.8 (s, C-3), 135.8, 139.1 (2s, Ar—C), 150 (br. s, NCOO), 153.7 (s, NC=N), 162 (br. s, NCOO), 170.7 (s, N=CPh$_2$), 171.2 (s, OOCH$_2$CH$_3$) ppm.

i) 3-(2-Amino-2-ethoxycarbonyl-ethyl)-2,5-dihydropyrrole-1-(N,N'-di-tert.-butoxycarbonyl) carboxamidine To a solution of 118 mg (0.2 mmol) 3-(2-benzhydrilideneamino-2-ethoxycarbonyl-ethyl)-2,5-dihydropyrrole-1-(N,N'-di-tert.-butoxycarbonyl) carboxamidine in 2 ml THF was added 1 ml 1N hydrochloric acid. The mixture was stirred at room temperature for 30 min. Water (5 ml) was added, the aqueous layer was separated and washed twice with ether. The aqueous layer was brought to pH=8.5 by addition of 1N NaHCO$_3$ and was extracted five times with ether. The combined ether layers were washed with brine, dried over MgSO$_4$ and evaporated. The residue was purified by flash chromatography (chloroform/methanol 20:1) to yield 79 mg (93%) 3-(2-amino-2-ethoxycarbonyl-ethyl)-2,5-dihydropyrrole-1-(N,N'-di-tert.-butoxycarbonyl) carboxamidine as a colorless oil.

$^1$H-NMR ($CDCl_3$, 300 MHz) d=1.22 (t, J=7.1 Hz, 3H, OCH$_2$CH$_3$), 1.45 [s, 18H, C(CH$_3$)$_3$], 2.33 (dd, $^2$J=16.6 Hz), $^3$J=8.1 Hz, 1H, CH$_a$H$_b$CHNH$_2$), 2.54 (dd, $^2$J=16.6 Hz, $^3$J=5.3 Hz, 1H, CH$_a$H$_b$CHNH$_2$), 3.54 (dd, $^3$J=8.1, 5.3 Hz, 1H, CH$_a$H$_b$CHNH$_2$), 4.13 (q, J=7.1 Hz 2H, OCH$_2$CH$_3$), 4.33 (br. m, 4H, 2-H, 5-H), 5.53 (br. m, 1H, 4-H) ppm.

$^{13}$C-NMR ($CDCl_3$, 75 MHz) d=13.9 (q, OCH$_2$CH$_3$), 27.9 [q, C(CH$_3$)$_3$], 34.1 (t, 3-CH$_2$), 52.7 (d, CHNH$_2$), 55.3, 56.9 (2d , C-2, C-5), 61.1 (t, OCH$_2$CH$_3$), ca 80 [2 br. s, C(CH$_3$)$_3$], 120.7 (d, C-4), 134.6 (s, C-3), 153.8 (s, NC=N), 174.6 (s, OOCH$_2$CH$_3$) ppm.

j) 3(2-tert.-Butoxycarbonyl-amino-2-ethoxycarbonyl-ethyl)-2,5-dihydropyrrole-1-(N,N'-di-tert.-butoxycarbonyl) carboxamidine To a solution of 79 mg (0.19 mmol) 3-(2-amino-2-ethoxycarbonyl-ethyl)-2,5-dihydropyrrole-1-(N,N'-di-tert.-butoxycarbonyl) carboxamidine in 1 ml dry acetonitrile was added 40 mg (0.3 mmol) ethyl diisopropylamine and 65 mg (0.3 mmol) di-tert.-butyl dicarbonate (Boc$_2$O) and the mixture was stirred for 16 h at room temperature. The solvent was evaporated and the residue was purified by flash chromatography (petrol ether/ethyl acetate 2:1) to yield 83 mg (76%) 3-(2-tert.-butoxycarbonyl-amino-2-ethoxycarbonyl-ethyl)-2,5-dihydropyrrole-1-(N,N'-di-tert.-butoxycarbonyl) carboxamidine as a colorless oil.

$^1$H-NMR (CDCl$_3$, 200 MHz) d=1.22 (t, J=7.1 Hz, 3H, OCH$_2$C$\underline{H}_3$), 1.42, 1.47, 1.48 [3 s, 9H each, C(CH$_3$)$_3$], 2.41–2.66 (br. m, 2H, 3-CH$_2$—), 4.17 (q, J=7.1 Hz, 2H, OC$\underline{H}_2$CH$_3$), 4.32 (br. m, 4H, 2-H, 5-H), 5.02 (br. m, 1H, CHNH), 5.52 (br. s, 1H, 4-H) ppm.

$^{13}$C-NMR (CDCl$_3$, 50 MHz) d=14.1 (q, OCH$_2$$\underline{C}$H$_3$), 28.1, 28.3, 28.5 [3q, C($\underline{C}$H$_3$)$_3$], 31.8 (t, 3-CH$_2$), 48.3 (d, CHNH), 52.0. 55.3 (2t, C-2, C-5), 61.6 (t, O$\underline{C}$H$_2$CH$_3$), 121.3 (d, C-4), 133.5 (s, C-3), 153.9 (s, N=C—N), 171.8 (s, COOEt) ppm. NCOO—, C(CH$_3$)$_3$-signals not visible due to line broadening.

k) 3-(2-tert.-Butoxycarbonyl-amino-2-carboxy-ethyl)-2,5-dihydropyrrole-1-(N,N'-di-tert.-butoxycarbonyl) carboxamidine To a solution of 267 mg (0.63 mmol) 3-(2-tert.-butoxycarbonyl-amino-2-ethoxycarbonyl-ethyl)-2,5-dihydropyrrole-1-(N,N'-di-tert.-butoxycarbonyl) carboxamidine in 5 ml THF/methanol/water 3:1:1 was added 50 mg (1.2 mmol) LiOH*H$_2$O. After 30 min stirring at room temperature no starting material could be detected by TLC. The mixture was made acidic by addition of 1N HCl, diluted with water and extracted three times with ether. The combined organic extracts were washed with brine, dried over MgSO$_4$ and evaporated. The residue was purified by flash-chromatography to give 98 mg (31%) of 3-(2-tert.-Butoxycarbonyl-amino-2-carboxy-ethyl)-2,5-dihydropyrrole-1-(N,N'-di-tert.-butoxycarbonyl) carboxamidine (Boc-Ada(Boc$_2$)-OH) as a colorless amorphous solid.

$^1$H-NMR (CDCl3, 300 MHz) δ=1.39, 1.44 [2s, 9H, 18H, C(CH$_3$)$_3$], 2.49–2.67 (br. m, 2H, 3-CH$_2$—), 4.33 (br. m, 4H, 2-H, 5-H), 5.30 (br. d, 1H, CHNH), 5.56 (br. s, 1H, 4-H) ppm.

$^{13}$H-NMR (CDCl3, 75 MHz) δ=27.7, 28.9, 28.0 [3q, C($\underline{C}$H$_3$)$_3$], 31.3 (t, 3-CH$_2$), 52.0 (d, CHNH), 55.3, 56.9 (2t, C-2, C-5), 80.0, 80.9 [2s, ($\underline{C}$(CH$_3$)$_3$], 121.1 (d, C-4), 133.6 (s, C-3), 153.2 (s, N=C—N), 155.2 (br. s, NCOO), 176.5 (s, COOH) ppm.

EXAMPLE 2

(±)-3-(2-Fluorenylmethoxycarbonyl-amino-2-hydroxycarbonyl-ethyl)-2,5-dihydropyrrole-1-(N,N'-di-tert.-butoxycarbonyl) carboxamidine [Fmoc-Ada(Boc)$_2$OH]

a) (±)-3-(2-Benzhydrylidene-2-tert.-butoxycarbonyl-ethyl-2,5-dihydropyrrole-1-carboxylic acid tert. butyl ester To a solution of lithium hexamethyldisilazide [freshly prepared at 0° C. from 1.53 g (9.5 mmol) hexamethyldisilazane and 4.09 g (9.5 mmol) n-BuLi, (2.32 mmol/g in hexanes)] in 20 ml THF was added at –78° C. a solution of 2.79 g (9.5 mmol) tert. butyl-N-(diphenylmethylene)-glycinate in 20 ml THF. The orange enolate solution was stirred for 30 min at –78° C., then a solution of 2.70 g (8.6 mmol) 3-acetoxymethyl-2,5-dihydro-pyrrole-1-carboxylic acid tert.-butylester and 243 mg (0.21 mmol) Pd(PPh$_3$)$_4$ in 20 ml THF was added dropwise. The reaction mixture was allowed to warm to room temperature over and was stirred for additional 12 h. The mixture was diluted with ether and quenched by addition of sat. NH$_4$Cl. The organic layer was washed with sat. NH$_4$Cl and brine, dried over MgSO$_4$ and evaporated. Purification by flash chromatography (ethyl acetate/petrol ether 1:10+0.5% triethylamine) gave 3.70 g (90%) 3-(2-benzhydrylidene-2-tert.-butoxycarbonyl-ethyl-2,5-dihydropyrrole-1-carboxylic acid tert.butyl ester as a slightly yellow oil.

$^1$H-NMR (CDCl$_3$, 300 MHz) d=1.41, 1.42 [2s, 9H each, C(CH$_3$)$_3$], 2.62–2.71 (m, 2H, 3-CH$_2$—), 3.80–4.10 (br. m, 4H, 2-H, 5-H, CHN), 5.41 (br. m, 1H, 4-H), 7.09–7.81 (m, 10 H, Ar—H) ppm.

$^{13}$C-NMR (CDCl$_3$, 75 MHz) d=27.8, 28.3 [2q, C($\underline{C}$H$_3$)$_3$], 33.0 (t, 3-CH$_2$), 52.7, 53.1, 54.5, 55.0 (4t, C-2, C-5)*, 64.2, 64.4 (2d, CH—NH$_2$)*, 78.9 [s, C(CH$_3$)$_3$], 81.07, 81.13 [2s, $\underline{C}$(CH$_3$)$_3$]*, 121.4, 121.5 (2d, C-4)*, 127.5, 127.6, 128.1, 128.2, 128.3, 128.4, 128.6, 128.7, 130.1 (9d, Ar—CH)*, 135.8, 135.9, 136.1 (3s, Ar—C)*, 139.2, 139.3 (s, C-3)*, 153.8, 153.9 (2s, NCOO)*, 170.1, 170.2 [2s, $\underline{C}$(CH$_3$)$_3$]170.4 (s, N=CPh$_2$) ppm.

HR-MS (FAB$^+$)

[M$^+$+H] C$_{29}$H$_{37}$N$_2$O$_4$ calc.: 477.2753 found: 477.2769

[M$^{30}$ +Na] C$_{29}$H$_{36}$N$_2$O$_4$Na calc.: 499.2573 found: 499.2570 b) (±)-3-(2-Amino-2-tert.-butoxycarbonyl-ethyl)-2,5-dihydropyrrole-1-carboxylic acid tert.-butyl ester To a solution of 1.57 g (3.3 mmol) 3-(2-benzhydrylidene-2-tert.-butoxycarbonyl-ethyl-2.5-dihydropyrrole-1-carboxylic acid tert. butyl ester in 10 ml THF and 5 ml water was added 5 ml glacial acetic acid and the mixture was stirred overnight at room temperature. THF was evaporated in vacuo, the residue was diluted with water and made alkaline by cautious addition of solid K$_2$CO$_3$ (or NH$_3$ solution). The mixture was extracted three times with ethyl acetate and dried over MgSO$_4$. Purification by flash chromatography (elution with CH$_2$Cl$_2$/MeOH 20:1) gave 1.03 g (100%) 3-(2-amino-2-tert.-butoxycarbonyl-ethyl)-2,5-dihydropyrrole-1-carboxylic acid tert.-butyl ester as a colorless, waxy solid.

$^1$H-NMR (CDCl$_3$, 300 MHz) d=1.41, 1.42 [2s, 9H each, C(CH$_3$)$_3$], 2.35 (dd, $^2$J=14.6 Hz, $^3$J=7.4 Hz, 1H, C$\underline{H}_a$H$_b$CHNH$_2$), 2.49 (dd, $^2$J=14.6 Hz, $^3$J=5.8 Hz, 1H, CH$_a$$\underline{H}_b$CHNH$_2$), 3.44 (dd, $^3$J=7.4, 5.8 Hz, 1H, CH$_a$H$_b$C$\underline{H}$NH$_2$), 4.04 (m, 4H, 2-H, 5-H), 5.49 (br. m, 1H, 4-H) ppm.

$^{13}$C-NMR (CDCl$_3$, 75 MHz) d=27.8, 28.3 [2q, C($\underline{C}$H$_3$)$_3$], 34.46, 34.52 (2t, 3-CH$_2$)*, 52.7, 53.0, 54.4, 54.6 (4d, C-2, C-5)*, 53.2 (d, CHNH$_2$), 79.0, 79.1, 81.18, 81.23 [4s, $\underline{C}$(CH$_3$)$_3$]*, 121.6, 122.0 (2d, C-4)*, 135.4, 135.6 (2s, C-3)*, 153.9 (s, NCOO), 174.2 (s, COOtBu)ppm.

HR-MS (FAB$^+$)

[M$^+$+H] C$_{16}$H$_{29}$N$_2$O$_4$ calc.: 313.2127 found: 313.2095 c) (±)-3-[2-(9-Fluorenylmethoxycarbonyl-amino)-2-tert.-butoxycarbonyl-ethyl]-2,5-dihydropyrrole-1-carboxylic acid tert.-butyl ester To a ice-cooled solution of 1.03 g (3.3 mmol) 3-(2-amino-2-tert.-butoxycarbonyl-ethyl)-2,5-dihydropyrrole-1-carboxylic acid tert.-butyl ester and 0.46 g (4.3 mmol) diisopropyl ethylamine 15 ml THF was added 0.98 g (3.8 mmol) 9-fluorenylmethyl chloroformate in one portion. The mixture was stirred at room temperature overnight. The mixture was diluted with ether, poured on ice-water and the aqueous layer was extracted three times with ether. The combined organic layers were dried (MgSO$_4$) and evaporated. Purification by flash chromatography (ethyl acetate/petrol ether 1:3) gave 1.70 g (97%) 3-[2-(9-fluorenylmethoxycarbonyl-amino)-2-tert.-butoxycarbonyl-ethyl]-2,5-dihydropyrrole-1-carboxylic acid tert.-butyl ester as a colorless, amorphous solid.

$^1$H-NMR (CDCl$_3$, 300 Hz) d=1.45 [s, 9H, C(CH$_3$)$_3$], 2.48–2.70 (br. m, 2H, C$\underline{H}_2$CHNH$_2$), 4.05 (br. m, 4H, 2-H, 5-H), 4.20 (t, 1H, C$\underline{H}$CH$_2$O), 4.41 (br. m, 3H, C$\underline{H}$NH, CHC$\underline{H}_2$O), 5.36 (br. m, 1H, NH), 5.49 (br. m, 1H, 4-H), 7.27–7.40 (m, 4H, Ar—H), 7.56–7.61 (m, 2H, Ar—H), 7.73–7.76 (m, 2H, Ar—H) ppm.

$^{13}$C-NMR (CDCl$_3$, 75 MHz) d=27.7, 28.3 [2q, C($\underline{C}$H$_3$)$_3$], 31.9, 32.2 (2t, 3-CH$_2$)*, 46.9 (d, $\underline{C}$HCH$_2$O), 52.6 (d, CHNH$_2$), 52.7, 53.0, 54.6 (1br. d, 2d, C-2, C-5)*, 66.7 (t, CH$\underline{C}$H$_2$O), 79.1, 79.2, 82.46, 82.51 [4s, $\underline{C}$(CH$_3$)$_3$]*, 119.8 (d, Ar—CH), 122.4, 122.8 (2d. C-4)*, 124.8, 127.3, 127.5 (3d, Ar—CH), 134.3 (br. s, C-3), 141.1, 143.6 (2s, Ar—C) 153.9, 155.4 (2s, NCOO), 170.5 (s, COOtBu) ppm.

HR-MS (FAB$^+$)

[M$^+$] C$_{31}$H$_{38}$N$_2$O$_6$ calc.: 535.2808 found: 535.2789

[M$^+$+Na] C$_{31}$H$_{38}$N$_2$O$_6$Na calc.: 557.2628 found: 557.2643 d) (±)-3-(2,5-Dihydro-1H-pyrrol-3-yl)-2-fluorenylmethoxycarbonylamino-propionic acid hydrochloride To a solution of 588 mg (1.1 mmol) 3-[2-(9-fluorenylmethoxycarbonyl-amino)-2-tert.-butoxycarbonyl-ethyl]-2,5-dihydropyrrole-1-carboxylic acid tert.-butyl ester and 376 mg (4 mmol) ethylene dithiol in 5 ml dioxane was added 5 ml 4N HCl in dioxane and the mixture was stirred at room temperature overnight. After 30 min a colorless solid began to precipitate, 20 ml of ether was added, the solid was filtered off, washed thoroughly with ether and dried in vacuo to give 433 mg (95%) (±)-3-(2,5-dihydro-1H-pyrrol-3-yl)-2-fluorenylmethoxycarbonylamino-propionic acid hydrochloride as a slightly colored powder.

$^1$H-NMR (CD$_3$OD, 300 MHz) d=2.56–2.80 (m, 2H, C$\underline{H}_2$CHNH$_2$), 3.99 (br. s, 4H, 2-H, 5-H), 4.21 (t, 1H, C$\underline{H}$CH$_2$O), 4.31–4.42 (m, 3H, C$\underline{H}$NH, CHC$\underline{H}_2$O), 5.36 (br. m, 1H, NH), 5.62 (br. s, 1H, 4-H), 7.28–7.41 (m, 4H, Ar—H), 7.63–7.68 (m, 2H, Ar—H), 7.77–7.80 (m, 2H, Ar—H) ppm.

$^{13}$C-NMR (CD$_3$OD, 75 MHz) d=31.5, (t, $\underline{C}$H$_2$CHNH), 48.3 (d, $\underline{C}$HCH$_2$O), 53.3, 53.5, 54.1 (3d, 2d, C-2, C-5, CH$_2$CHNH), 67.9 (t, CH$\underline{C}$H$_2$O), 120.9 (d, Ar—CH), 122.0 (d, C-4), 126.2, 128.1, 128.8 (3d, Ar—CH), 136.6 (s, C-3), 142.6., 145.2 (2s, Ar—C), 158.5 (s, NCOO), 174.4 (s, COOH) ppm.

e) (±)-3-(2-Fluorenylmethoxycarbonyl-amino-2-hydroxycarbonyl-ethyl)-2,5-dihydropyrrole-1-(N,N'-di-tert.-butoxycarbonyl) carboxamidine To a suspension of 400 mg (0.96 mmol) (±)-3-(2,5-dihydro-1H-pyrrol-3-yl)-2-fluorenylmethoxycarbonylamino-propionic acid hydrochloride in 5 ml acetonitrile were added 258 mg (2 mmol) ethyl diisopropylamine, followed by 298 mg (0.96 mmol) N,N'-bis-tert.-butyloxycarbonyl-1H-pyrazole-1-carboxamidine. The heterogenous mixture was stirred at room temperature overnight and was then diluted with ethyl acetate. The mixture was acidified with acetic acid and water was added. The aqueous layer was extracted three times with ethyl acetate, the combined organic layers were washed with brine, dried and evaporated to dryness. Flash chromatography (petrol ether/ethyl acetate 1:1+1% acetic acid gave 123 mg (21%) (±)-3-(2-fluorenylmethoxycarbonyl-amino-2-hydroxycarbonyl-ethyl)-2,5-dihydropyrrole-1-(N,N'-di-tert.-butoxycarbonyl) carboxamidine as a slightly yellow amorphous solid.

$^1$H-NMR (CD$_3$OD, 300 MHz) d=1.45 [s, 18H, C(CH$_3$)$_3$], 2.57–2.79 (br. m, 2H, C$\underline{H}_2$CHNH$_2$), 4.05 (br. m, 4H, 2-H, 5-H), 4.20 (t, 1H, C$\underline{H}$CH$_2$O), 4.41 (br. m, 3H, C$\underline{H}$NH, CHC$\underline{H}_2$O), 5.36 (br. m, 1H, NH), 5.49 (br. m, 1H, 4-H), 7.24–7.37 (m, 4H, Ar—H), 7.54–7.57 (m, 2H, Ar—H), 7.70–7.73 (m, 2H, Ar—H) ppm.

$^{13}$C-NMR (CD$_3$OD, 75 MHz) d=27.7, 27.9 [2q, C(CH$_3$)$_3$], 31.3 (t, $\underline{C}$H$_2$CHNH), 46.9 (d, $\underline{C}$HCH$_2$O), 52.6 (d, CH$_2$$\underline{C}$HNH), 55.5, 57.0 (2d, C-2, C-5), 66.8 (t, CH$\underline{C}$H$_2$O), 81.1 [br s, $\underline{C}$(CH$_3$)$_3$], 119.7 (d, Ar—CH), 121.2 (d, C-4), 124.9, 126.9, 127.5 (3d, Ar—CH), 133.6 (s, C-3), 141.1, 143.6 (2s, Ar—C) 153.0, 155.8 (2s, NCOO), 176.5 (s, COOtBu) ppm.

HR-MS (FAB$^+$)

[M$^+$] C$_{33}$H$_{41}$N$_4$O$_8$ calc.: 621.2924 found: 621.2881

EXAMPLE 3

Ada-SAW

The title compound was synthesized by solid-phase methodology on a SyRo II multiple peptide synthesizer (MultiSynTech, Bochum) on a 0.03 mmol scale using Fmoc-L-Trp-trityl-polystyrene(1%)divinylbenzene resin (Fmoc-L-Trp-TCP; loading: 0.57 mmol/g; PepChem, Tübingen) as starting material. The α-amino groups of the proteinogenic amino acids Ala and Ser were protected by 9-fluorenylmethoxycarbonyl (Fmoc), the side chain hyrdroxy group of Ser by tert.-butyl. The non-proteinogenic amino acid Ada was used as Boc-Ada(Boc$_2$)-OH (from example 1). The Fmoc-protected amino acids were coupled in a 6-fold excess for 30 min in DMF. TBTU (1 eq) and NMM (1 eq) were used as activating reagents. Cleavage of the Fmoc group was carried out in piperidine/dimethylformamide (1:1 v/v) for 2×10 min. Coupling of Boc-Ada(Boc$_2$)-OH was performed manually in DMF within 1 h by using 0.048 mmol of the protected amino acid (1.65-fold excess) and equimolare amounts of TBTU and NMM for activation. The peptide was cleaved from the resin with 750 ul of acetic acid/trifluoroethanol/dichloromethane (30:10:70) within 2 h. After washing five times with 150 ul of the same solvent mixture the filtrates were combined, diluted with 10 ml heptane and concentrated. This procedure was repeated twice in order to remove the acetic acid completely. The oily residue was dissolved in 5 ml 4 N hydrogen chloride in dioxane. To this solution 270 ul ethanedithiol were added and the mixture was stirred for 3 h at room temperature. Then the solvent was removed and the residue dissolved in heptane and concentrated again several times until the ethanedithiol was almost completely removed. The crude peptide was lyophilized from tert.-butanol/water (1:1) and purified by preparative HPLC to yield 9.5 mg Ada-SAW as colorless lyophilisate (purity by HPLC >90%). ESI-MS: m/z 543.3 M$^+$

EXAMPLE 4

Ada-Ava-W

The title peptide was prepared in the same manner as example 3 starting from 50 mg (0.03 mmol) Fmoc-L-Trp-TCP resin using Fmoc protected aminovaleric acid. Yield: 6.2 mg Ada-Ava-W as colorless lyophilisate (purity by HPLC >90%). ESI-MS: m/z 484.3 M$^+$

EXAMPLE 5

Ada-Aba-W

The title peptide was prepared in the same manner as example 3 starting from 50 mg (0.03 mmol) Fmoc-L-Trp- TCP resin using Fmoc protected aminobutyric acid. Yield: 4.8 mg Ada-Aba-W as colorless lyophilisate (purity by HPLC >90%). ESI-MS: m/z 470.3 M$^+$

EXAMPLE 6

T-Ada-SAW

The title compound was synthesized by solid-phase methodology on a SyRo II multiple peptide synthesizer (MultiSynTech, Bochum) on a 0.03 mmol scale using Fmoc-L-Trp-trityl-polystyrene(1%)divinylbenzene resin (Fmoc-L-Trp-TCP; loading: 0.57 mmol/g; PepChem, Tübingen) as starting material. The α-amino groups of the proteinogenic amino acids Ala and Ser were protected by 9-fluorenylmethoxycarbonyl (Fmoc), the side chain hydroxy group of Ser by tert.-butyl. The non-proteinogenic amino acid Ada was used as Fmoc-Ada(Boc$_2$)-OH (from example2). The Fmoc-protected amino acids were coupled in a 6-fold excess for 30 min in DMF. TBTU (1 eq) and NMM (1 eq) were used as activating reagents. Cleavage of the Fmoc group was carried out in piperidine/dimethylformamide (1:1v/v) for 2×10 min. Coupling of Boc-Ada(Boc$_2$)-OH and Thr was performed manually in DMF within 1 h by using 0.048 mmol of the protected amino acid Boc-Ada(Boc$_2$)-OH (1.65-fold excess) and a 6 fold excess in the case of Thr. Equimolar amounts of TBTU and NMM were used for activation. The peptide was cleaved from the resin with 750 ul of acetic acid/trifluoroethanol/dichloromethane (30:10:70) within 2 h. After washing five times with 150 ul of the same solvent mixture the filtrates were combined, diluted with 10 ml heptane and concentrated. This procedure was repeated twice in order to remove the acetic acid completely. The oily residue was dissolved in 5 ml 4 N hydrogen chloride in dioxane. To this solution 270 ul ethanedithiol were added and the mixture was stirred for 3 h at room temperature. Then the solvent was removed and the residue dissolved in heptane and concentrated again several times until the ethanedithiol was almost completely removed. The crude peptide was lyophilized from tert.-butanol/water (1:1) and purified by preparative HPLC to yield 2.6 mg T-Ada-SAW as colorless lyophilisate (purity by HPLC >98%). ESI-MS: m/z 644.3 M$^+$

EXAMPLE 7

T-Ada-Ava-W

The title peptide was prepared in the same manner as example 6 starting from 50 mg (0.03 mmol) Fmoc-L-Trp-TCP resin using Fmoc protected aminovaleric acid. Yield: 2.7 mg T-Ada-Ava-W as colorless lyophilisate (purity by HPLC >95%). ESI-MS: m/z 585.3 M$^+$

EXAMPLE 8

T-Ada-Aba-W

The title peptide was prepared in the same manner as example 6 starting from 50 mg (0.03 mmol) Fmoc-L-Trp-TCP resin using Fmoc protected aminobutyric acid. Yield: 2.7 mg T-Ada-Aba-W as colorless lyophilisate (purity by HPLC >95%). ESI-MS: m/z 585.3 M$^+$

EXAMPLE 9

Biological Activity

Compounds of general formula (I) were tested in an in vitro DNA-synthesis assay. The cells used were primary cultures of osteoblasts from fetal rat calvarias. The experiments were performed in an analogous manner as published in Pfeilschifter et al., Endocrinology 126, 703 (1990).

| Compound | Example | Biological activity in % compared to control (100%) | | | | |
| --- | --- | --- | --- | --- | --- | --- |
| | | 0.001 µg/ml | 0.01 µg/ml | 0.1 µg/ml | 1.0 µg/ml | 10 µg/ml |
| Ada-SAW | (3) | 122 | 148 | 199 | 162 | 188 |
| Ada-Ava-W | (4) | 116 | 152 | 182 | 183 | 229 |
| Ada-Aba-W | (5) | 173 | 184 | 228 | 223 | 261 |

What is claimed is:

1. A compound of the formula

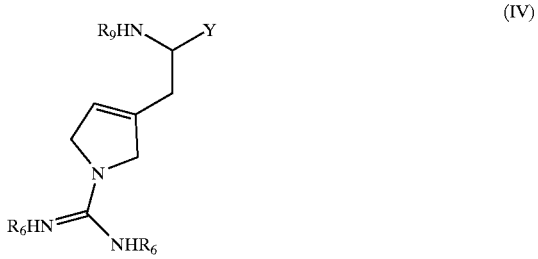

(IV)

wherein
R$_6$ is a protecting group;
R$_9$ is Fmoc; and
Y is COOH or COO-alkyl, wherein the alkyl group has 1 to 4 carbon atoms.

2. The compound of claim 1, wherein R$_6$ is a benzoyl group, an alkyloxycarbonyl group or a benzyloxycarbonyl group.

3. A compound of the formula

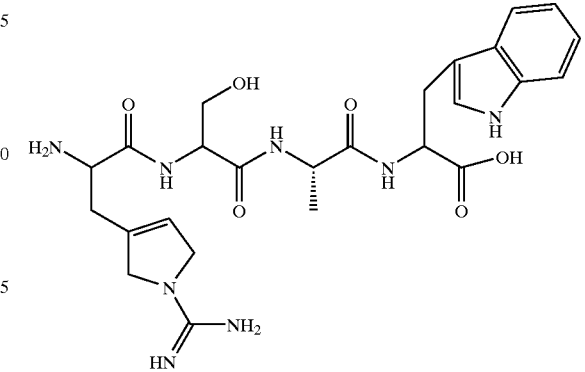

4. A compound of the formula

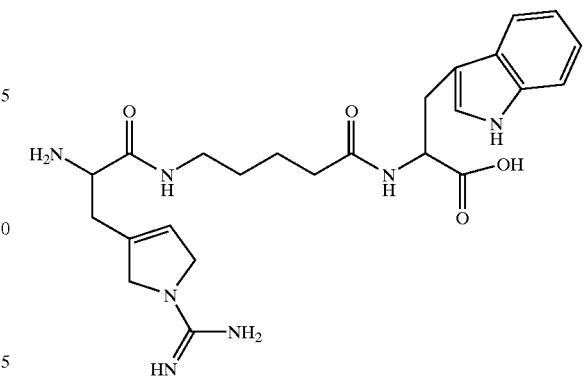

5. A compound of the formula
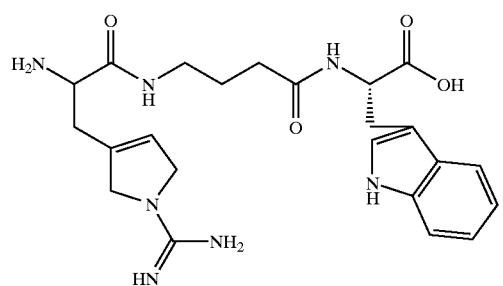
7. A compound of the formula
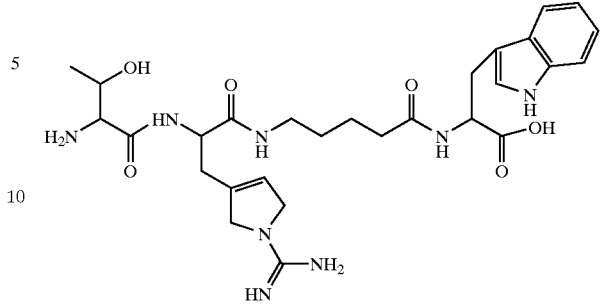
6. A compound of the formula
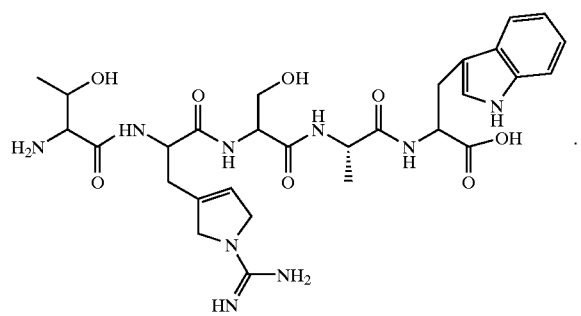
8. A compound of the formula
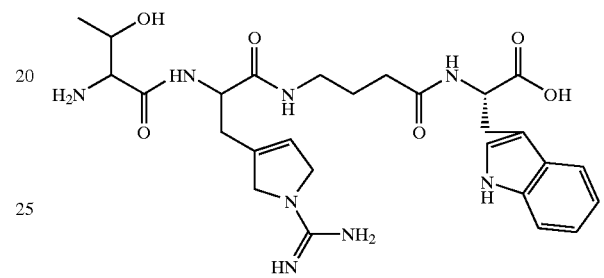
* * * * *